(12) United States Patent
Kubo

(10) Patent No.: US 11,978,209 B2
(45) Date of Patent: May 7, 2024

(54) ENDOSCOPE SYSTEM, MEDICAL IMAGE PROCESSING DEVICE, AND OPERATION METHOD THEREFOR

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 84 days.

(21) Appl. No.: 17/809,241

(22) Filed: Jun. 27, 2022

(65) Prior Publication Data

US 2022/0414885 A1 Dec. 29, 2022

(30) Foreign Application Priority Data

Jun. 28, 2021 (JP) .................................. 2021-107104
Dec. 1, 2021 (JP) .................................. 2021-195541

(51) Int. Cl.
*G06T 7/00* (2017.01)
*A61B 1/00* (2006.01)
*A61B 1/06* (2006.01)
*G06T 3/40* (2006.01)
*G06T 7/11* (2017.01)
(Continued)

(52) U.S. Cl.
CPC ...... *G06T 7/0016* (2013.01); *A61B 1/000094* (2022.02); *A61B 1/0005* (2013.01); *A61B 1/0638* (2013.01); *G06T 3/40* (2013.01); *G06T 7/11* (2017.01); *G06T 7/337* (2017.01); *G06T 11/203* (2013.01); *G06V 10/761* (2022.01); *A61B 1/0004* (2022.02);
(Continued)

(58) Field of Classification Search
CPC . G06T 7/0016; G06T 3/40; G06T 7/11; G06T 7/337; G06T 11/203; G06T 2207/20104; G06T 2207/20212; G06T 2207/30096; A61B 1/000094; A61B 1/0005; A61B 1/0638; A61B 1/0004; G06V 10/761; G06V 2201/03
See application file for complete search history.

(56) References Cited

U.S. PATENT DOCUMENTS

| | | | | |
|---|---|---|---|---|
| 2011/0002520 A1* | 1/2011 | Suehling | ............... | G06T 7/0012 |
| | | | | 382/154 |
| 2019/0034800 A1* | 1/2019 | Shiratani | ................ | G06N 3/042 |
| 2021/0233298 A1 | 7/2021 | Usuda | | |

FOREIGN PATENT DOCUMENTS

WO 2020/090731 A1 5/2020

* cited by examiner

*Primary Examiner* — Chong Wu
(74) *Attorney, Agent, or Firm* — Studebaker & Brackett PC

(57) ABSTRACT

A medical image processing device a reference image that is a medical image with which boundary line information related to a boundary line that is a boundary between an abnormal region and a normal region and landmark information related to a landmark that is a characteristic structure of the subject are associated and a captured image that is the medical image captured in real time, detects the landmark from the captured image, calculates a ratio of match between the landmark included in the reference image and the landmark included in the captured image, estimates a correspondence relationship between the reference image and the captured image on the basis of the ratio of match and information regarding the landmarks included in the reference image and the captured image, and generates a superimposition image in which the boundary line associated with the reference image is superimposed on the captured image on the basis of the correspondence relationship.

17 Claims, 27 Drawing Sheets

(51) Int. Cl.
*G06T 7/33* (2017.01)
*G06T 11/20* (2006.01)
*G06V 10/74* (2022.01)

(52) U.S. Cl.
CPC ............... *G06T 2207/20104* (2013.01); *G06T 2207/20212* (2013.01); *G06T 2207/30096* (2013.01); *G06V 2201/03* (2022.01)

ENDOSCOPE SYSTEM, MEDICAL IMAGE PROCESSING DEVICE, AND OPERATION METHOD THEREFOR

CROSS-REFERENCE TO RELATED APPLICATIONS

This application claims priority under 35 U.S.C § 119(a) to Japanese Patent Applications No. 2021-107104 filed on 28 Jun. 2021 and No. 2021-195541 filed on 1 Dec. 2021. The above application is hereby expressly incorporated by reference, in its entirety, into the present application.

BACKGROUND OF THE INVENTION

1. Field of the Invention

The present invention relates to an endoscope system, a medical image processing device, and an operation method therefor capable of supporting an operation such as endoscopic submucosal dissection.

2. Description of the Related Art

Endoscopic submucosal dissection (ESD) makes it possible to resect tumors or the like with a size to which endoscopic mucosal resection (EMR) cannot be applied and thus to complete an operation without selecting a highly invasive surgery. ESD is performed endoscopically, and thus has the advantage of being minimally invasive. On the other hand, the gastrointestinal tract is extremely thin, 5 to 7 mm thick in the stomach and 3 to 5 mm thick in the large intestine, and advanced techniques are required for doctors who perform ESD.

There is a technique capable of showing a lesion region to assist an operator during an operation. For example, there is a medical image processing device that detects a region of interest including a lesion, and superimposes coordinates of a boundary between the region of interest and a region of uninterest, coordinates of a position inside the region of interest and along the boundary, or coordinates of the center of gravity of the region of interest on the region of interest (WO2020/090731A, corresponding to US2021/233298A1).

SUMMARY OF THE INVENTION

Advances in image processing have made it possible to show a region or a boundary line of a differentiated lesion on an image, but in a method of determining a range of a lesion for each frame, a range displayed as the lesion also changes over time. That is, since an image captured in real time changes from moment to moment, it is difficult to accurately determine a boundary line between an abnormal region and a normal region of an observation target in real time, and a displayed boundary line is inaccurate depending on imaging conditions. In a case of applying ESD, it is difficult to determine a boundary line in low-magnification observation (distant view observation) that can give a bird's-eye view of the entire lesion, and thus it is necessary to perform high-magnification observation (near view observation) in which a part of the lesion is enlarged. In light of the above circumstances, there is a demand for a technique capable of recognizing an accurate boundary line determined from an image captured under optimum conditions in real time. There is a need for a technique capable of checking how a boundary line diagnosed in the past has changed on the current real-time image.

The present invention provides an endoscopic system, a medical image processing device, and a method of operating therefor capable of recognizing an accurate boundary line in real time.

According to an aspect of the present invention, there is provided a medical image processing device including a processor, in which the processor acquires a medical image obtained by imaging a subject with an endoscope, acquires a reference image that is the medical image with which boundary line information related to a boundary line that is a boundary between an abnormal region and a normal region and landmark information related to a landmark that is a characteristic structure of the subject are associated, acquires a captured image that is the medical image captured in real time, detects the landmark from the captured image, calculates a ratio of match between the landmark included in the reference image and the landmark included in the captured image, estimates a correspondence relationship between the reference image and the captured image on the basis of the ratio of match and information regarding the landmarks included in the reference image and the captured image, and generates a superimposition image in which the boundary line associated with the reference image is superimposed on the captured image on the basis of the correspondence relationship.

It is preferable that the captured image and the reference image are medical images picked up at the same magnification. It is preferable that the captured image is the medical image captured in a distant view, and the reference image is the medical image captured in a near view.

It is preferable that the captured image is the medical image captured to include a part of the abnormal region, and the reference image is the medical image including the entire abnormal region, and the superimposition image in which a part of the boundary line associated with the reference image is superimposed on the captured image is generated.

It is preferable that the reference image is generated by connecting enlarged medical images which are medical images in which a part of the abnormal region is captured in a near view.

It is preferable that the processor, in a case where the reference image is formed of a first enlarged medical image and a second enlarged medical image captured at a position different from that of the first enlarged medical image, generates the reference image by connecting the first enlarged medical image and the second enlarged medical image on the basis of a common relationship between the landmark information and the boundary line information associated with the first enlarged medical image and the landmark information and the boundary line information associated with the second enlarged medical image It is preferable that processor identifies the abnormal region and the normal region, and sets the boundary line. The boundary line is preferably set through a user operation.

It is preferable that the reference image is the medical image captured by illuminating the subject with special light, and the captured image is the medical image captured by illuminating the subject with normal light.

It is preferable that the captured image in which the landmark is detected and the captured image on which the boundary line is superimposed are the captured images that are captured at the same time point.

It is preferable that the captured image in which the landmark is detected and the captured image on which the boundary line is superimposed are the captured images that are captured at different time points. It is preferable that calculation of the ratio of match is continued until an end instruction is given.

It is preferable that the processor performs control for generating a display image, displaying the superimposition image in a first display section of the display image, and displaying the reference image in a second display section different from the first display section of the display image.

It is preferable that the processor acquires an enlarged captured image as the captured image, identifies the abnormal region and the normal region included in the enlarged captured image, and sets the boundary line, detects the landmark from the enlarged captured image, and generates the reference image by associating the enlarged captured image with the boundary line information related to the boundary line and the landmark information related to the landmark.

It is preferable that the processor generates the superimposition image, and in a case where the abnormal region and the normal region included in the captured image related to the superimposition image on which the boundary line is superimposed are identified in a case where there is an update instruction, and an update boundary line is set with the boundary between the abnormal region and the normal region as the boundary line, and in a case where there is an update determination instruction, updates the boundary line superimposed on the captured image with the update boundary line as a determined update boundary line.

According to another aspect of the present invention, there is provided an operation method for a medical image processing device, including a step of acquiring a medical image obtained by imaging a subject with an endoscope; a step of acquiring a reference image that is the medical image with which boundary line information related to a boundary line that is a boundary between an abnormal region and a normal region and landmark information related to a landmark that is a characteristic structure of the subject are associated; a step of acquiring a captured image that is the medical image captured in real time; a step of detecting the landmark from the captured image; a step of calculating a ratio of match between the landmark included in the reference image and the landmark included in the captured image; a step of estimating a correspondence relationship between the reference image and the captured image on the basis of the ratio of match and information regarding the landmarks included in the reference image and the captured image; and a step of generating a superimposition image in which the boundary line associated with the reference image is superimposed on the captured image on the basis of the correspondence relationship.

According to still another aspect of the present invention, there is provided an endoscope system including the medical image processing device and the endoscope.

According to the present invention, it is possible to recognize an accurate boundary line in real time.

DESCRIPTION OF THE PREFERRED EMBODIMENTS

Figure 1:
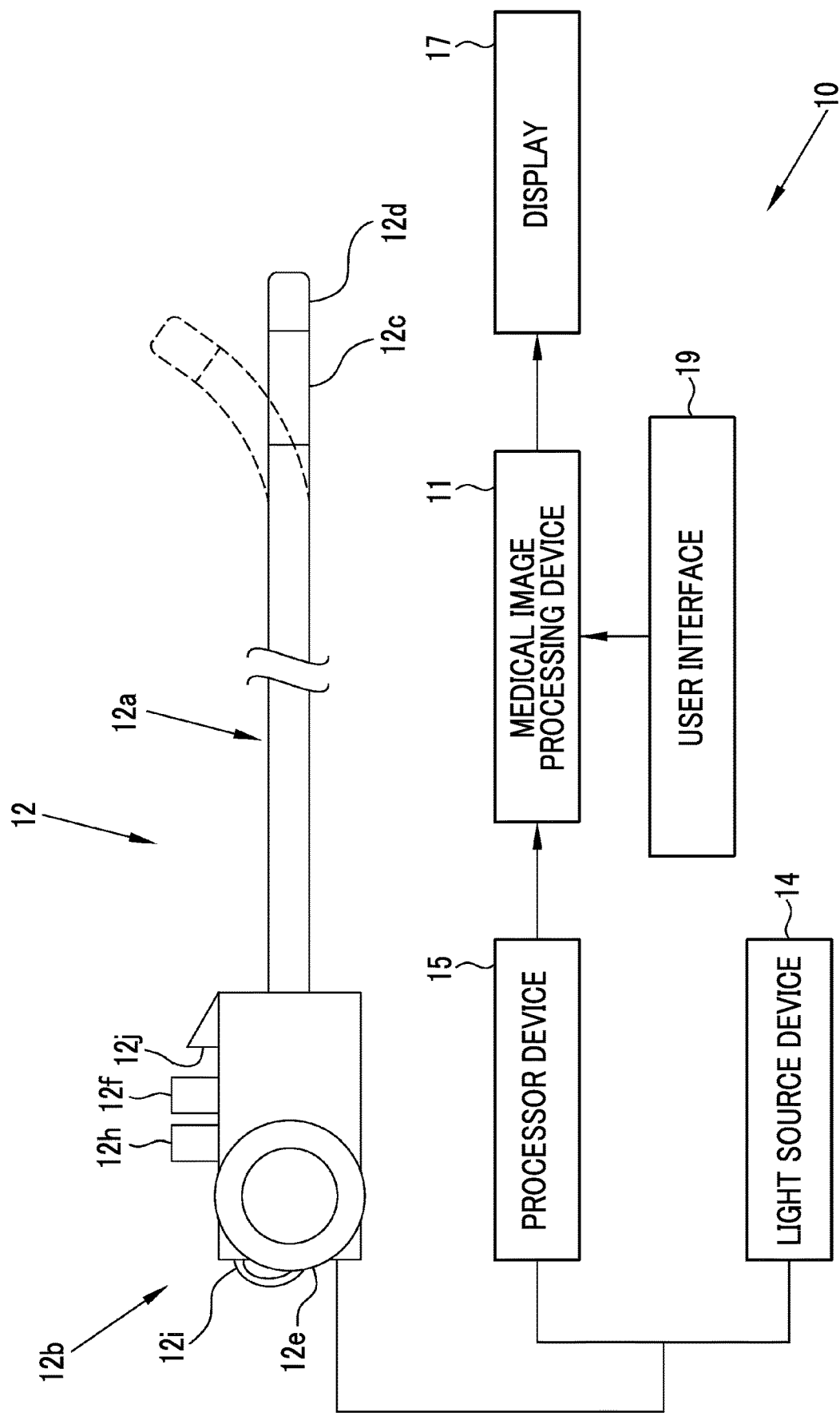
FIG. 1 is an explanatory diagram of a configuration of an endoscope system.

An endoscope system 10 includes an endoscope 12, a light source device 14, a processor device 15, a medical image processing device 11, a display 17, and a user interface 19. The medical image processing device 11 is connected to the endoscope system 10 via the processor device 15. The endoscope 12 is optically connected to the light source device 14 and electrically connected to the processor device 15.

The endoscope 12 is provided on an insertion part 12a to be inserted into the body of an observation target, an operating part 12b provided at a base end portion of the insertion part 12a, and a bendable part 12c and a tip part 12d provided at a distal end side of the insertion part 12a. The bendable part 12c is bent by operating an angle knob 12e of the operating part 12b. The tip part 12d is directed in a desired direction in a case where the bendable part 12c is bent. A forceps channel (not shown) for inserting a treatment tool or the like is provided from the insertion part 12a to the tip part 12d. The treatment tool is inserted into the forceps channel from a forceps port 12j.

Inside the endoscope 12, an optical system for forming a subject image and an optical system for irradiating a subject with illumination light are provided. The operating part 12b is provided with an angle knob 12e, a mode selector switch 12f, a still image acquisition instruction switch 12h, and a zoom operating part 12i. The mode selector switch 12f is used for an observation mode selection operation. The still image acquisition instruction switch 12h is used for an instruction for acquiring a still image. The zoom operating part 12i is used to operate a zoom lens 42.

The light source device 14 generates illumination light. The display 17 displays a medical image. The medical image includes a reference image that is a medical image in which a captured image that is a medical image captured by the endoscope 12 in real time, information regarding a boundary line that is a boundary between an abnormal region and a normal region, which will be described later, and a landmark that is a characteristic structure of a subject are associated with each other, and a superimposition image in which a boundary line is superimposed on a captured image. The real time does not represent an exact time or the exact same time, but refers to a time including the latest fixed period in one endoscopy. The abnormal region refers to a region in which an abnormality is observed in an observation target, such as a region in which a tumor is present or a region in which inflammation is observed. The normal region refers to a region other than the abnormal region in which no abnormality is observed. The abnormal region may be defined as a "tumor region", the normal region may be defined as a "non-tumor region", and only a region where the tumor is identified may be defined as the abnormal region, for example, a region where inflammation around the tumor is observed may be included in the normal region.

The user interface 19 includes a keyboard, a mouse, a touch pad, a microphone, a tablet terminal 241, a touch pen 242, and the like, and has a function of receiving input operations such as function settings. The processor device 15 performs system control on the endoscope system 10 and image processing and the like on an image signal transmitted from the endoscope 12.

Figure 2:
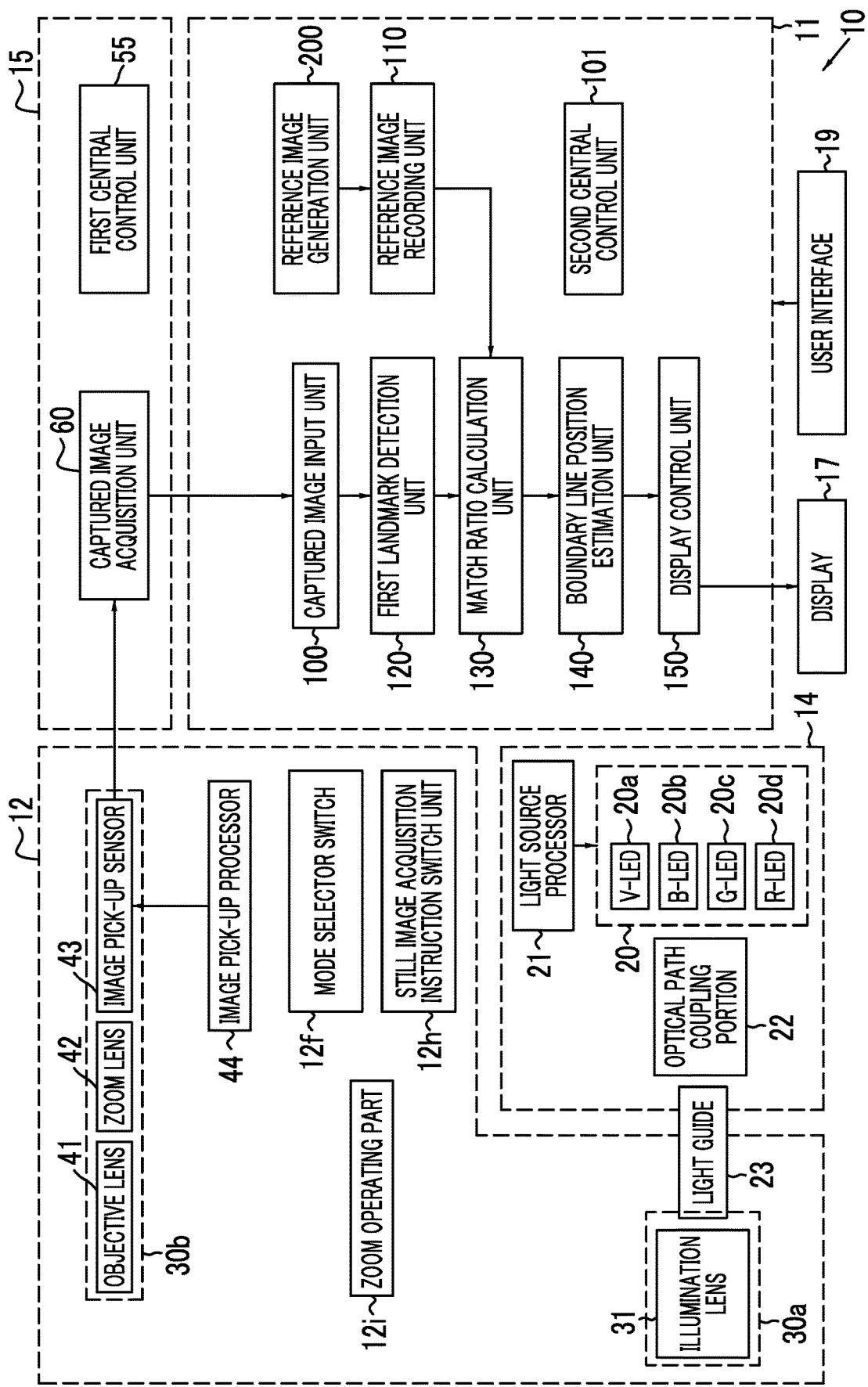
FIG. 2 is a block diagram showing a function of the endoscope system.

In FIG. 2, the light source device 14 includes a light source unit 20 and a light source processor 21 that controls the light source unit 20. The light source unit 20 has, for example, a plurality of semiconductor light sources, each of that is turned on or off, and in a case where the light source unit 20 is turned on, a light emission amount of each semiconductor light source is controlled such that illumination light for illuminating an observation target is emitted. The light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d. The light source unit 20 may be built in the endoscope 12, and the light source control unit may be built in the endoscope 12, or may be built in the processor device 15.

The endoscope system 10 includes a mono-emission mode, a multi-emission mode, a boundary line display mode, a reference image generation mode, and a boundary line update mode, which are switched by the mode selector switch 12f. The mono-emission mode is a mode in which illumination light having the same spectrum is continuously applied to illuminate an observation target. The multi-emission mode is a mode in which a plurality of illumination light beams having different spectra are applied while being switched therebetween according to a specific pattern to illuminate an observation target. The illumination light includes normal light (broadband light such as white light) used for observing the entire observation target by giving brightness to the entire observation target, or special light used for emphasizing a specific region of the observation target. In the mono-emission mode, switching to illumination light having another spectrum may be performed by operating the mode selector switch 12f. For example, switching may be performed with the normal light as first illumination light and the special light as second illumination light, or switching may be performed with the special light as first illumination light and the normal light as second illumination light.

Figure 3:
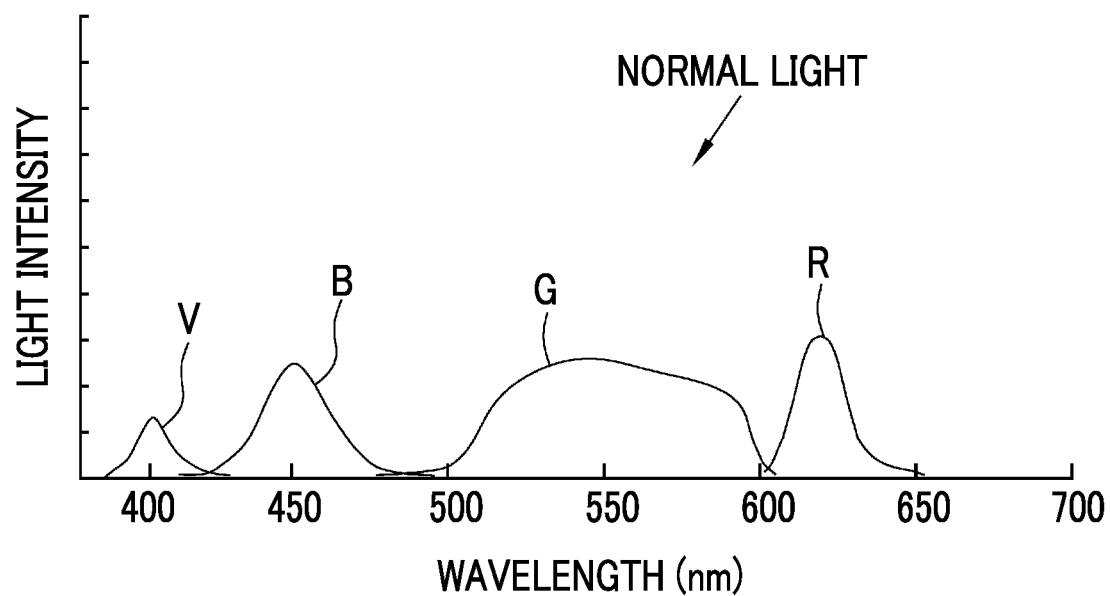
FIG. 3 is a graph showing spectra of violet light V, blue light B, green light G, and red light R in normal light.
Figure 4:
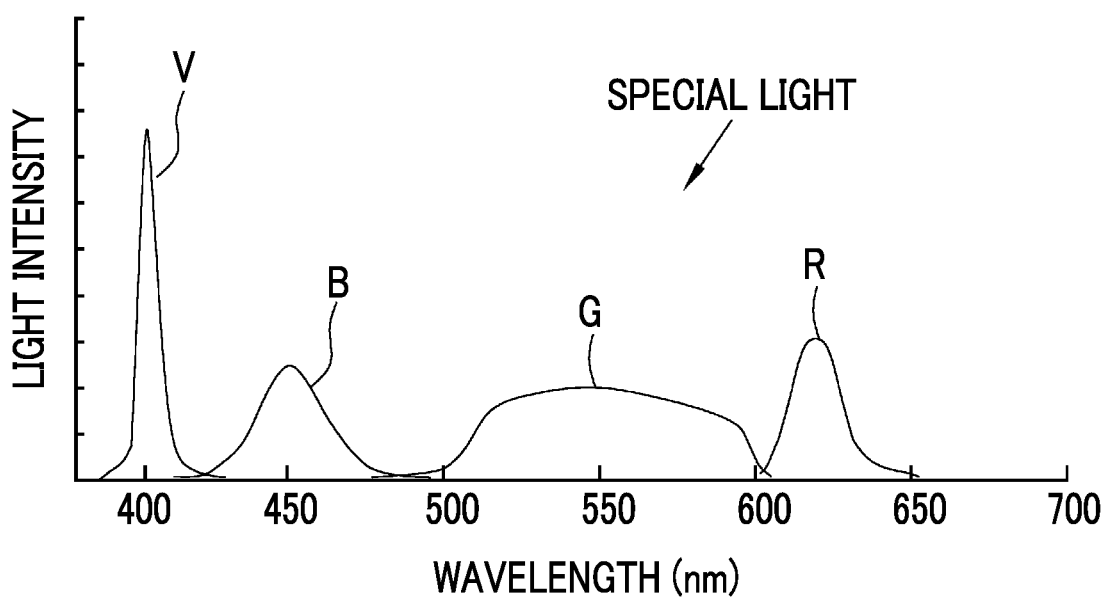
FIG. 4 is a graph showing spectra of violet light V, blue light B, green light G, and red light R in special light.

As shown in FIG. 3, in a case where the normal light is emitted, the V-LED 20a generates violet light V having a central wavelength of 405±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm. As shown in FIG. 4, special light in which an amount of the violet light V is larger than an amount of light of other blue light B, green light G, and red light R may be used.

The boundary line display mode is a mode in which, in a case where a tumor is found in a subject, a superimposition image in which a boundary line in a reference image in which an accurate boundary line is defined at a boundary between an abnormal region and a normal region in advance is superimposed on a captured image picked up in real time is generated and displayed on the display 17 to be shown to a user such that incision of the mucous membrane in ESD is supported. The reference image generation mode is a mode in which a reference image is generated by using a captured image. The boundary line update mode is a mode in which a boundary line is updated while displaying a superimposition image in which a boundary line in a reference image is superimposed on a captured image.

The light source processor 21 independently controls amounts of light of four colors such as the violet light V, the blue light B, the green light G, and the red light R. In the case of the mono-emission mode, illumination light having the same spectrum is continuously emitted for each frame. In the first illumination observation mode, a first illumination light image having a natural color is displayed on the display 17 by causing normal light such as white light (first illumination light) to illuminate an observation target and picking up an image thereof. The first illumination light and the second illumination light may be switched in the mono-emission mode, and a second illumination light image emphasizing a specific structure is displayed on the display 17 by causing special light (second illumination light) to illuminate an observation target and picking up an image thereof. The first illumination light image and the second illumination light image are a kind of examination image.

Light used for performing ESD is usually the first illumination light. In a case where it is desired to check an infiltration range of a lesion part before performing ESD, the second illumination light may be used. In the boundary line display mode, it may be selected whether a medical image is obtained according to a light emission pattern in either the mono-emission mode or the multi-emission mode, or either the first illumination light image or the second illumination light image is obtained as a medical image according to a light emission pattern in the mono-emission mode.

Figure 5:
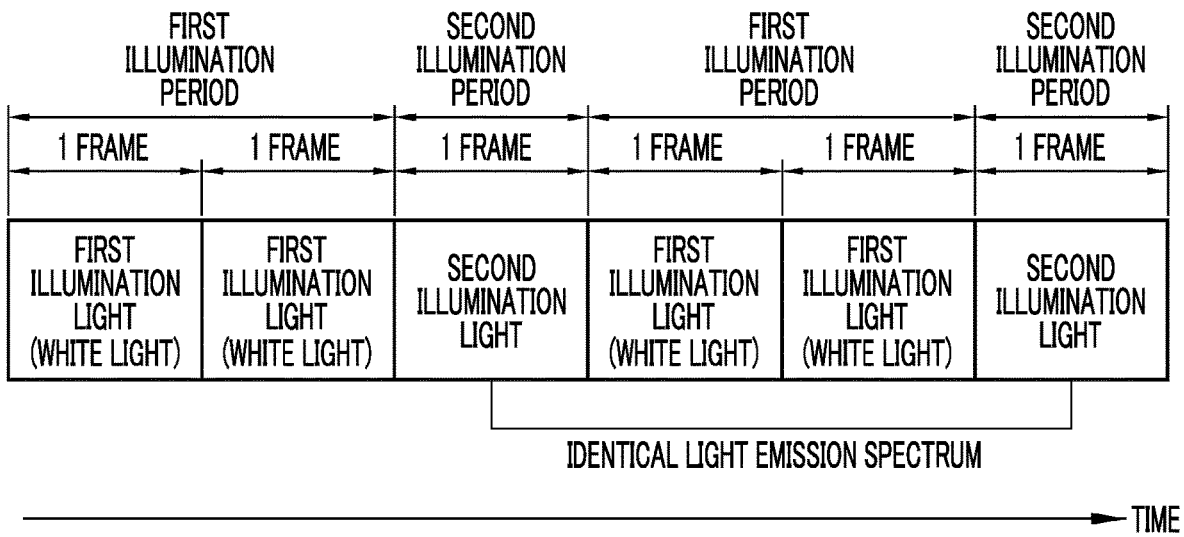
FIG. 5 is an explanatory diagram showing a first light emission pattern in an image analysis mode.
Figure 6:
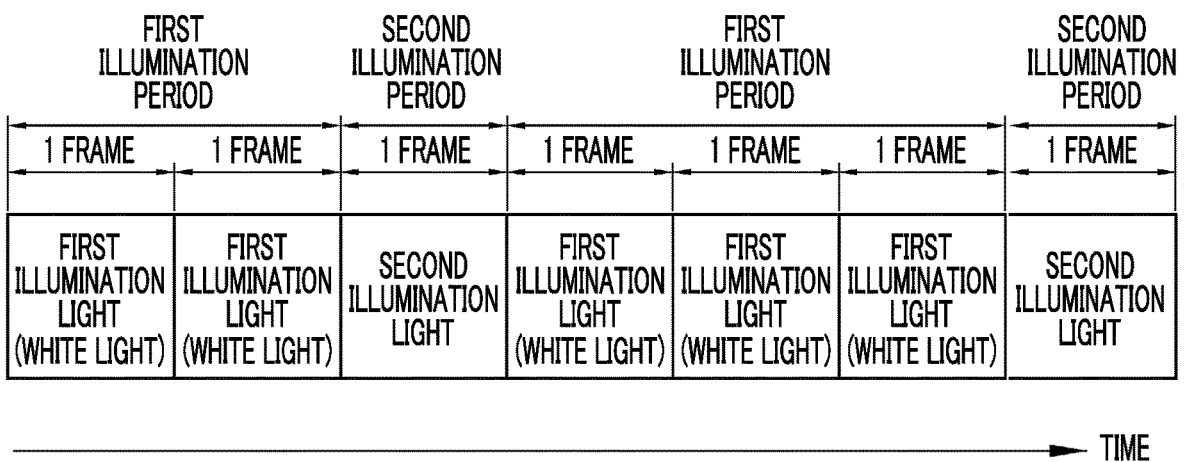
FIG. 6 is an explanatory diagram showing a second light emission pattern in the image analysis mode.

On the other hand, in the case of the multi-emission mode, control is performed such that amounts of the violet light V, the blue light B, the green light G, and the red light R are changed according to a specific pattern. For example, the first illumination light and the second illumination light are switched therebetween, as a light emission pattern, as shown in FIG. 5, as in a first light emission pattern in which the number of frames in a first illumination period in which the first illumination light illuminates a subject is the same as that in each first illumination period and, as shown in FIG. 6, a second light emission pattern in which the number of frames in the first illumination period is different from that in each first illumination period. In FIGS. 5 and 6, the arrow represents a direction of passage of time. The frame means a time from when an image pick-up sensor (not shown) provided at the tip part 12d of the endoscope starts receiving return light from an observation target to when output of accumulated charge signals on the basis of the received light is completed. The second illumination period is a period in which the subject is illuminated by the second illumination light.

The light emitted by each of the LEDs 20a to 20d (refer to FIG. 2) is incident to a light guide 23 via an optical path coupling portion 22 configured with a mirror, a lens, and the like. The light guide 23 propagates light from the optical path coupling portion 22 to the tip part 12d of the endoscope 12.

An illumination optical system 30a and an image pick-up optical system 30b are provided at the tip part 12d of the endoscope 12. The illumination optical system 30a has an illumination lens 31, and the illumination light propagated by the light guide 23 is applied to an observation target via the illumination lens 31. In a case where the light source unit 20 is built in the tip part 12d of the endoscope 12, the light source unit 20 emits light toward a subject via the illumination lens of the illumination optical system without by using the light guide. The image pick-up optical system 30b has an objective lens 41 and an image pick-up sensor 43. Light from an observation target due to the irradiation of the illumination light is incident to the image pick-up sensor 43 via the objective lens 41 and the zoom lens 42. Consequently, an image of the observation target is formed on the image pick-up sensor 43. The zoom lens 42 is a lens for enlarging the observation target, and is moved between the telephoto end and the wide end by operating the zoom operating part 12i.

The image pick-up sensor 43 is a primary color sensor, and includes three types of pixels such as a blue pixel (B pixel) having a blue color filter, a green pixel (G pixel) having a green color filter, and a red pixel (R pixel) having a red color filter.

The image pick-up sensor 43 is preferably a charge-coupled device (CCD) or a complementary metal oxide semiconductor (CMOS). The image pick-up processor 44 controls the image pick-up sensor 43. Specifically, an image signal is output from the image pick-up sensor 43 by the image pick-up processor 44 reading out a signal of the image pick-up sensor 43. The output image signal is transmitted to a captured image acquisition unit 60 of the processor device 15.

The captured image acquisition unit 60 performs various types of signal processing such as a defect correction process, an offset process, a demosaic process, a matrix process, white balance adjustment, a gamma conversion process, and a YC conversion process on the received image signal. Next, image processing including a 3×3 matrix process, a gradation transformation process, a color conversion process such as three-dimensional look up table (LUT) processing, a color emphasis process, and a structure emphasis process such as spatial frequency emphasis is performed.

In a case where a user wants to acquire a captured image as a still image, by operating the still image acquisition instruction switch 12h, a signal related to a still image acquisition instruction is sent to the endoscope 12, the light source device 14, and the processor device 15, and thus a still image is acquired and stored in a still image storage unit (not shown).

In the processor device 15, a first central control unit 55 configured with an image control processor operates a program in a program memory to realize a function of the captured image acquisition unit 60.

The captured image generated by the captured image acquisition unit 60 is transmitted to the medical image processing device 11. The medical image processing device 11 includes a captured image input unit 100, a reference image recording unit 110, a first landmark detection unit 120, a match ratio calculation unit 130, a boundary line position estimation unit 140, a display control unit 150, a reference image generation unit 200, and a second central control unit 101 (refer to FIG. 2).

In the medical image processing device 11, the second central control unit 101 configured with an image analysis processor operates a program in a program memory to realize functions of the captured image input unit 100, the reference image recording unit 110, the first landmark detection unit 120, the match ratio calculation unit 130, the boundary line position estimation unit 140, the display control unit 150, and the reference image generation unit 200.

Figure 7:
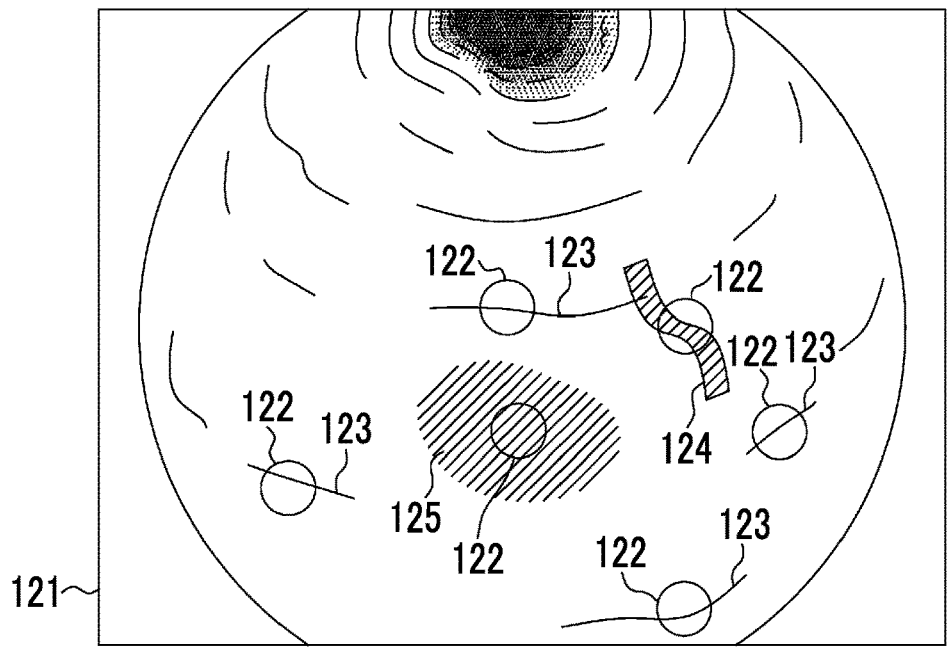
FIG. 7 is an image diagram showing an example of a captured image in which a landmark is detected.

In the case of the boundary line display mode, the captured image is transmitted to the captured image input unit 100 of the medical image processing device 11 (refer to FIG. 2). In the case of the boundary line display mode, the captured image input unit 100 transmits the captured image to the first landmark detection unit 120. As shown in FIG. 7, the first landmark detection unit 120 detects a landmark that is a characteristic structure of the subject from the captured image 121 picked up in real time (in FIG. 7, the landmark is surrounded and indicated by a circle 122). Landmarks include gastrointestinal folds 123, blood vessels 124, glandular ductal structures, as well as lesions 125 (indicated by diagonal lines in FIG. 7), structures highlighted by a fluorescent agent, and the like. The fluorescent agent is, for example, indocyanine green (ICG). Hereinafter, in order to prevent the drawings from becoming complicated, a leader line and a reference numeral are attached to any one of the circles 122 indicating the landmarks, unless otherwise specified.

Figure 8:
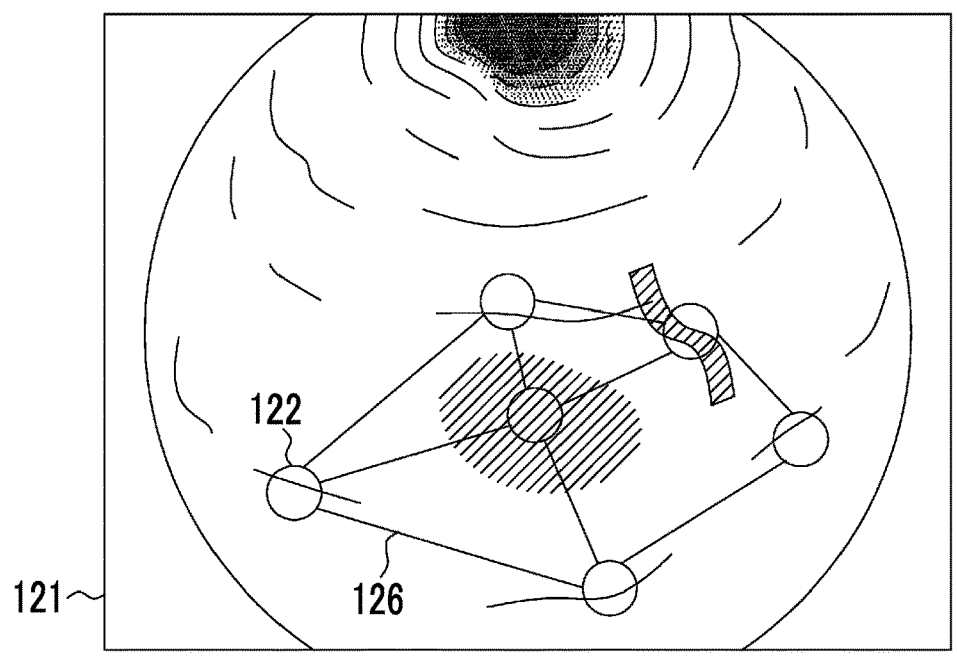
FIG. 8 is an image diagram showing an example of a captured image in which landmarks are connected via a link line.

The first landmark detection unit 120 detects the landmark and further acquires position information of the landmark. As shown in FIG. 7, in a case where a plurality of landmarks are detected from the captured image 121 through the detection process, it is preferable that the landmarks can be distinguished from each other. For example, each landmark may be given a distinction number for distinction. As shown in FIG. 8, it is preferable that the landmarks (indicated by the circles 122) are connected to each other via a link line 126, pieces of position information of the landmarks are associated with each other, and a positional relationship between the landmarks in the captured image 121 is recorded.

Figure 9:
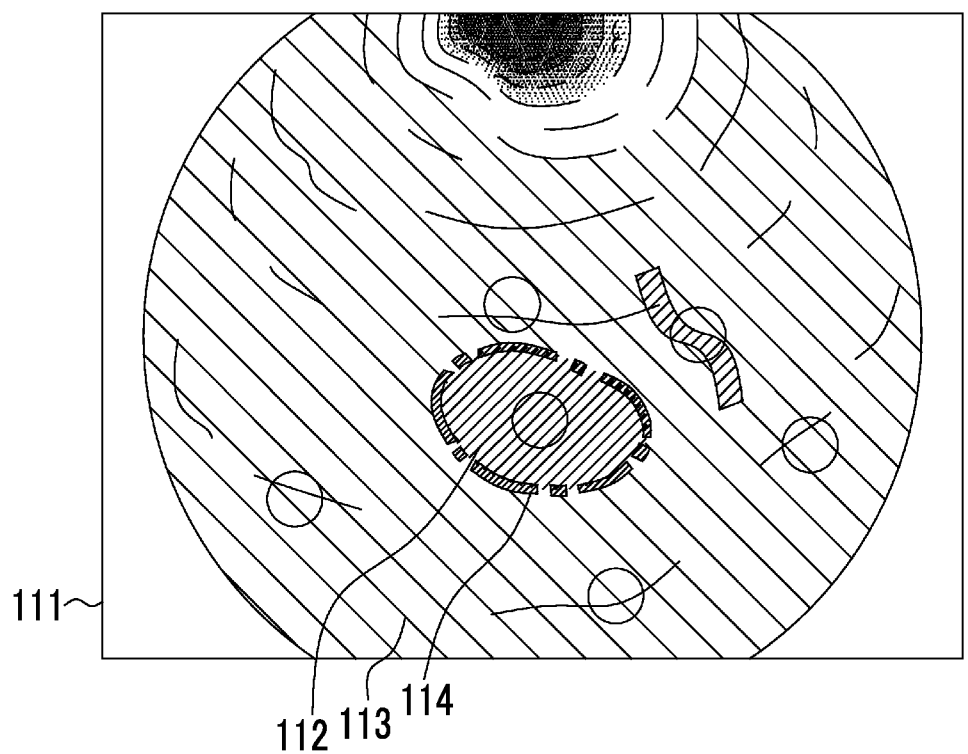
FIG. 9 is an image diagram showing an example of a reference image in which a boundary line is shown at a boundary between an abnormal region and a normal region.

The captured image in which the landmark is detected is transmitted to the match ratio calculation unit 130. In addition to the captured image in which the landmark is detected, a reference image 111 with which boundary line information related to a boundary line 114 (indicated by a dot chain line in FIG. 9) that is a boundary between an abnormal region 112 and a normal region 113 as shown in FIG. 9 and landmark information related to the landmark are associated is transmitted to the match ratio calculation unit 130 from the reference image recording unit 110. The reference image is a medical image previously recorded by a user in the reference image recording unit 110, in which the accurate boundary line 114 is set in advance at the boundary between the abnormal region 112 and the normal region 113. The boundary line information includes position information of the boundary line related to the boundary line. The landmark information includes position information of the landmark associated with the reference image, related to the landmark, and a positional relationship between the respective landmarks connected via the link line 126 (not shown in FIG. 9). It is preferable that the boundary line information and the landmark information are associated with each other by connecting the boundary line to each landmark via the link line 126.

Figure 10:
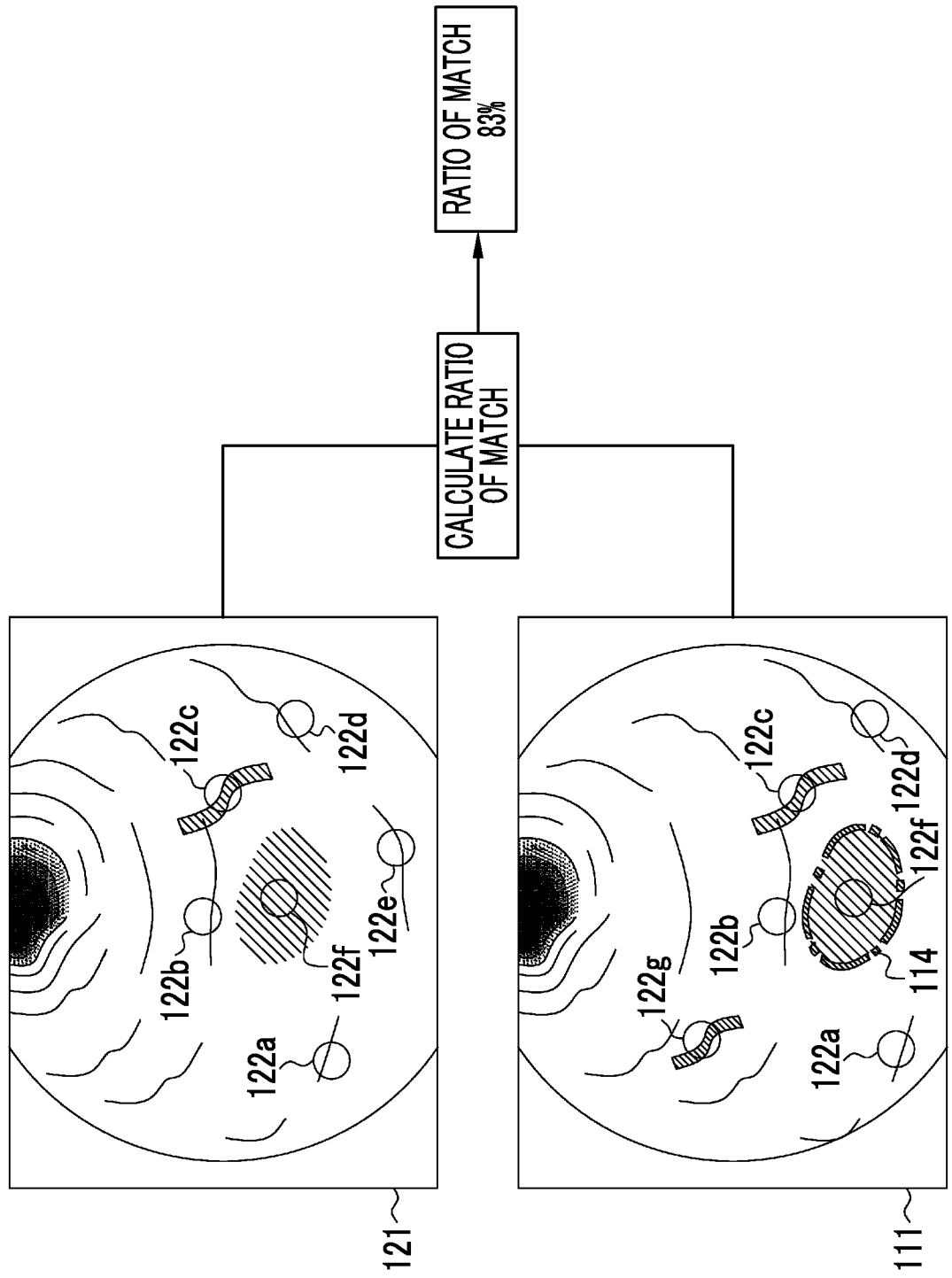
FIG. 10 is an explanatory diagram showing an example of calculating the ratio of match between a reference image and a captured image.

As shown in FIG. 10, the match ratio calculation unit 130 compares the reference image 111 with the captured image 121, and calculates a ratio of match. The ratio of match is a value indicating how much a landmark associated with the reference image 111 is included in a landmark detected from the captured image 121. In the example in FIG. 10, a ratio of match between landmarks included in the captured image 121 (locations are indicated by the circles 122*a*, 122*b*, 122*c*, 122*d*, 122*e*, and 122*f*) and landmarks included in the reference image 111 (locations are indicated by circles 122*a*, 122*b*, 122*c*, 122*d*, 122*f*, and 122*g*) is calculated. In this case, since the captured image 121 includes landmarks other than one landmark (circle 122 *g*) included in the reference image 111, the captured image 121 includes five of the six landmarks included in the reference image. Therefore, in the example in FIG. 10, for example, a ratio of match is 83% (rounded to the nearest whole number).

Figure 11:
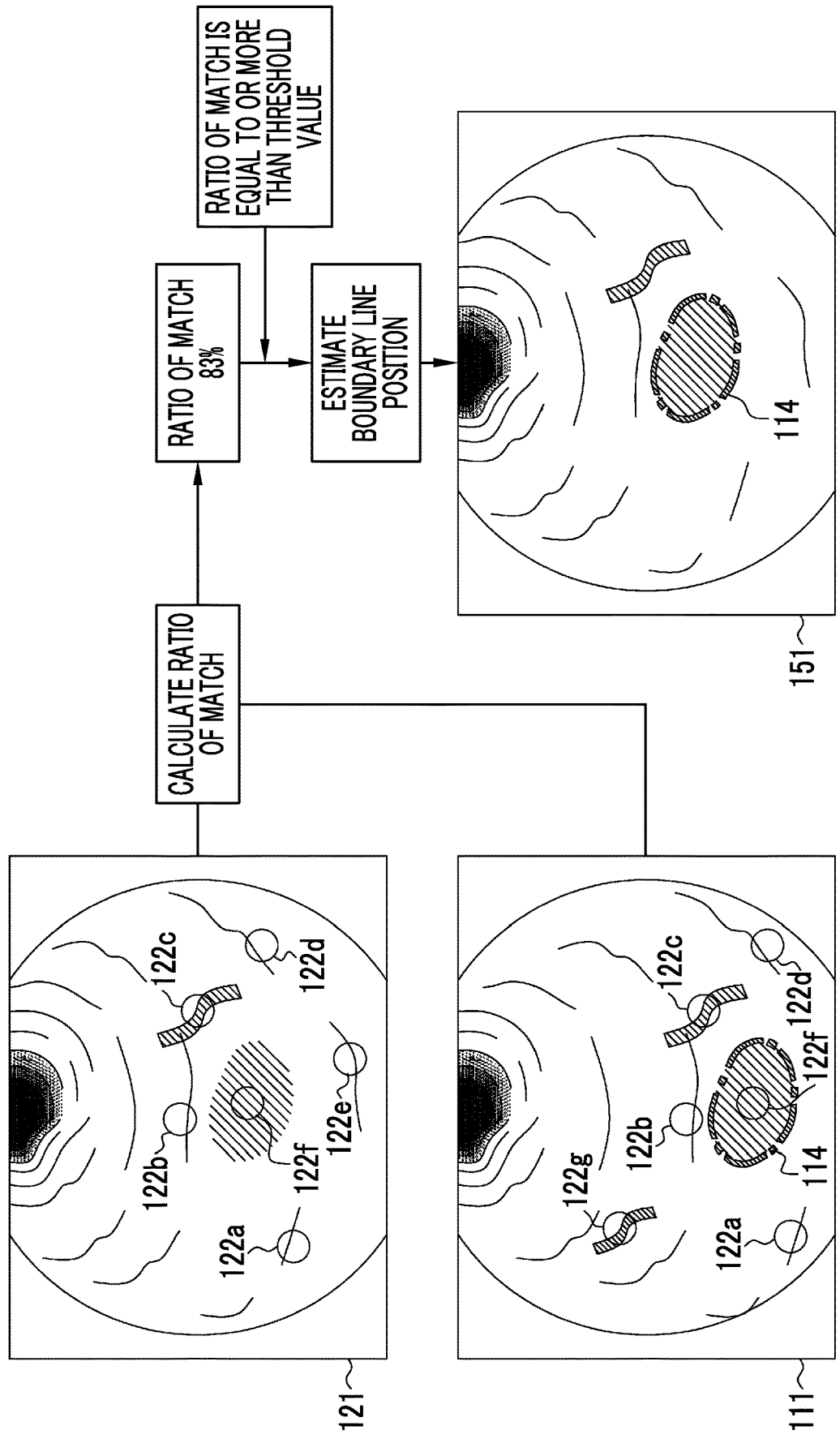
FIG. 11 is an explanatory diagram showing generation of a superimposition image.

As shown in FIG. 11, in a case where the ratio of match is equal to or more than a threshold value, the boundary line position estimation unit 140 estimates a correspondence relationship between the reference image and the captured image on the basis of the position information of the landmark detected from the captured image and the positional relationship between the respective landmarks, and the position information of the landmark associated with the reference image, the positional relationship between the respective landmarks, and the position information of the boundary line. The correspondence relationship is transmitted to the display control unit 150. Any threshold value for a ratio of match may be set. The correspondence relationship between the reference image and the captured image is a relationship in which a landmark on the captured image matching each landmark on the reference image is recognized from the position information of the landmark on the reference image and the captured image, and a part of the captured image corresponding to the boundary line is estimated from the positional relationship between the landmarks connected via the link line 126 on the reference image and the positional relationship between the landmarks connected via the link line 126 on the captured image.

The display control unit 150 generates a superimposition image 151 in which the boundary line 114 associated with the reference image 111 is superimposed on the captured image, as shown in FIG. 11, on the basis of the correspondence relationship in the reference image 111 and the captured image 121. The superimposition image 151 is a medical image in which the boundary line 114 associated with the reference image 111 is superimposed on the captured image 121 that is captured in real time.

With the above configuration, an accurate boundary line associated with the reference image is superimposed on the captured image picked up in real time by using the positional relationship between the landmarks, and thus the most probable boundary line can be checked in real time. Since it is possible to visually recognize how different the boundary line in the reference image is from that in the real-time image, it is possible to check expansion or contraction of an infiltration range of the tumor that has changed from the past to the present by comparing the reference image that is the past medical image with the captured image that is the current medical image.

Figure 12:
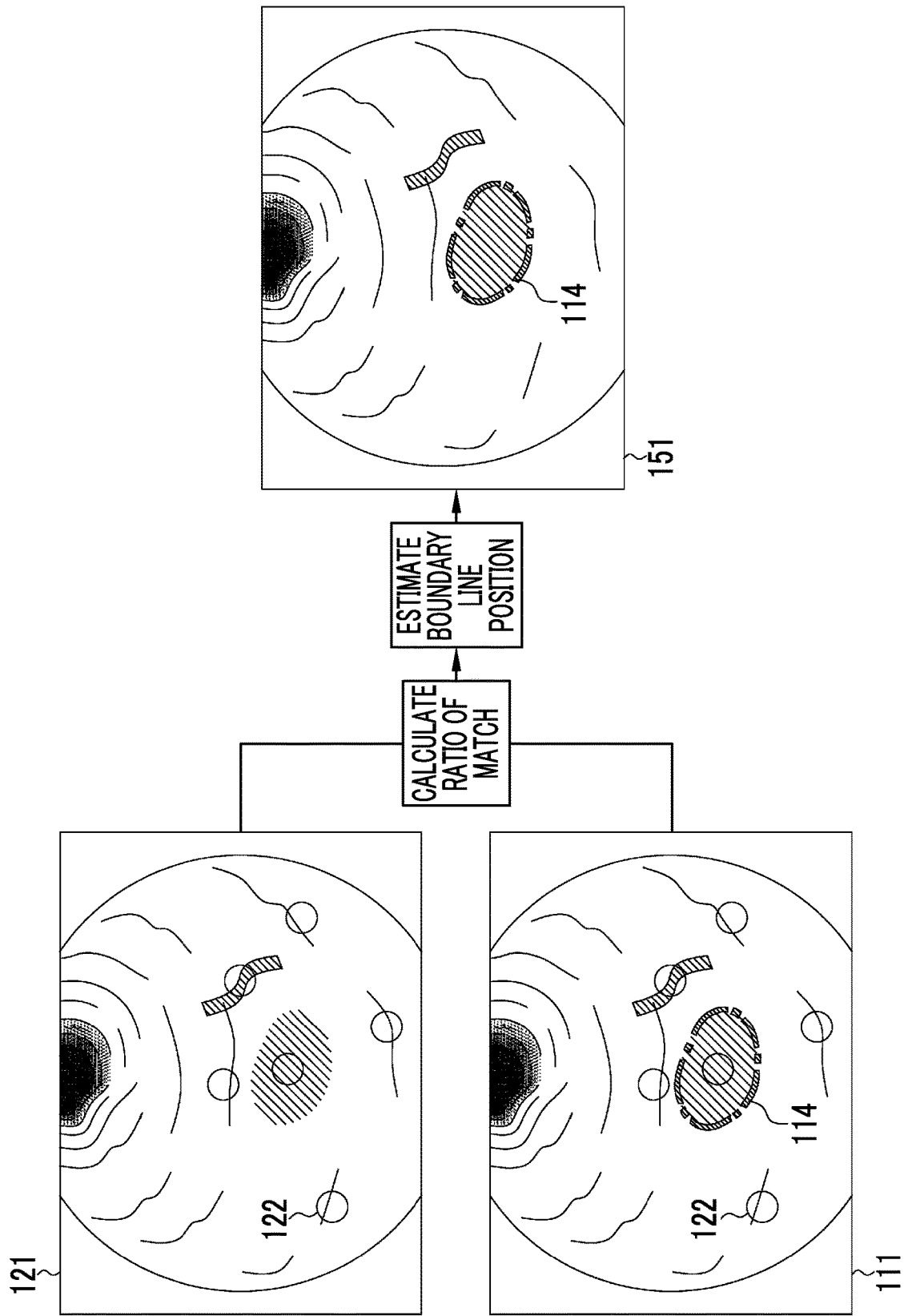
FIG. 12 is an explanatory diagram showing generation of a superimposition image when a captured image and a reference image are captured at the same magnification.

As shown in FIG. 12, the superimposition image is preferably created in a case where the captured image 121 and the reference image 111 are captured at the same magnification. In a case where the captured image 121 and the reference image 111 are acquired at the same magnification, the boundary line 114 can be accurately superimposed. Even in a case where a scene of the captured image changes due to ESD treatment such as marking on the mucous membrane or local injection of a local injection solution, an accurate boundary line can be displayed by using the positional relationship between the landmarks.

Figure 13:
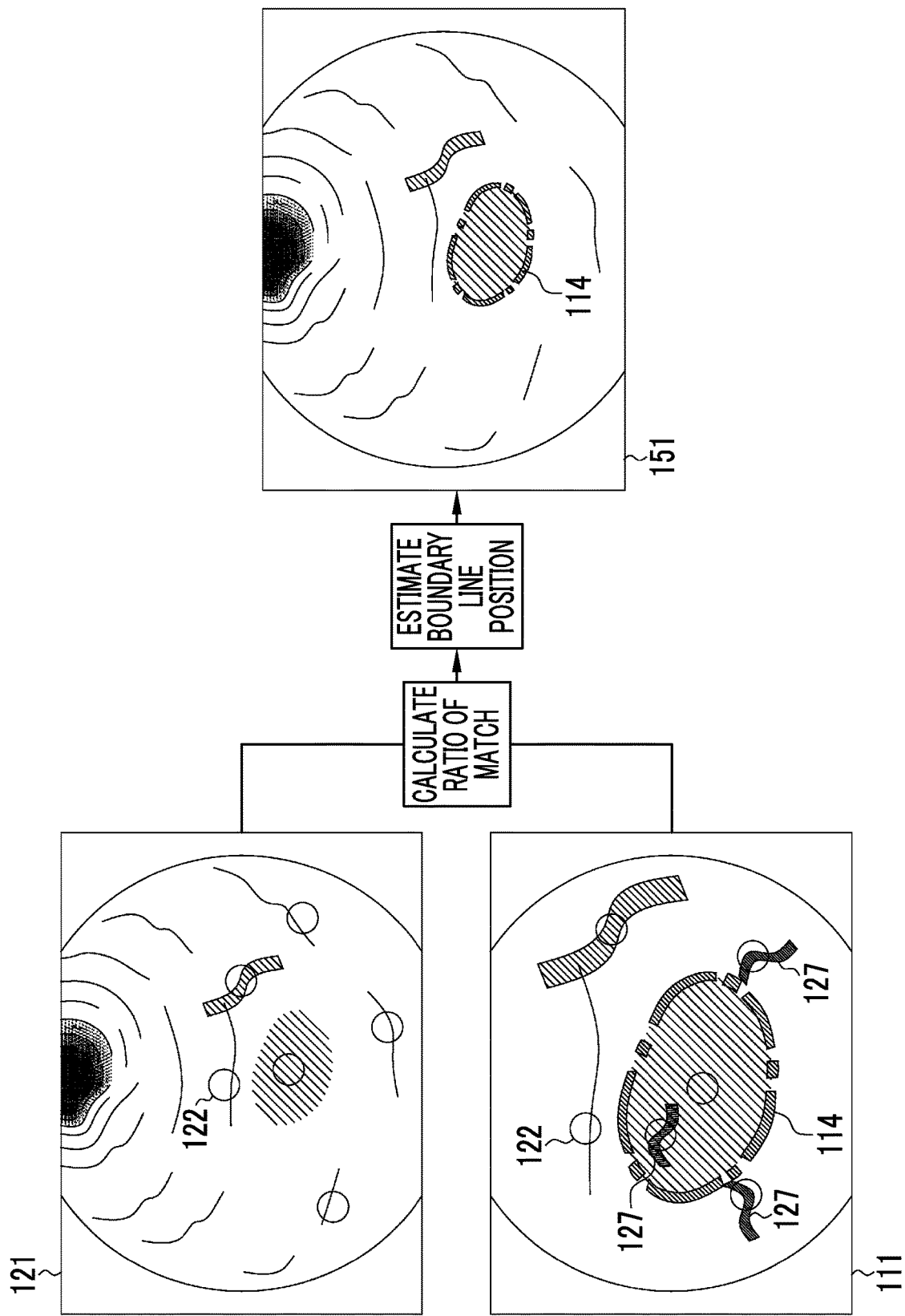
FIG. 13 is an explanatory diagram showing generation of a superimposition image in a case where a captured image is observed in a distant view and a reference image is captured in a near view.

As shown in FIG. 13, it is preferable to create the superimposition image 151 in a case where the captured image 121 is a medical image captured in a distant view and the reference image 111 is a medical image captured in a near view. In this case, the captured image 121 is captured at a lower magnification than that of the reference image 111. By estimating a position where the boundary line is superimposed on the basis of the positional relationship between the landmarks (indicated by the circles 122) included in the reference image 111, which matches the landmarks in the captured image 121, the boundary line 114 can be superimposed on the captured image 121 captured in a distant view. In a case of defining the boundary between the abnormal region and the normal region, it may be difficult to set the boundary line 114 unless a mucosal structure or a microvessel 127 is observed in detail by using a medical image captured in a near view. In a case where near-view imaging in a near view is required to set the boundary line, it is even more difficult to determine the accurate boundary line 114 in distant-view imaging that allows a bird's-eye view of the entire lesion. In such a case, in a case where there is a landmark that can be identified in both a medical image captured in a near view and a medical image captured in a distant view, even in a case where a captured image is acquired in distant-view imaging in real time at a distance where a boundary line cannot be determined, the boundary line 114 can be estimated by using a correspondence relationship between the boundary line and the landmark, and the boundary line can be displayed on the captured image 121 captured in a distant view.

Figure 14:
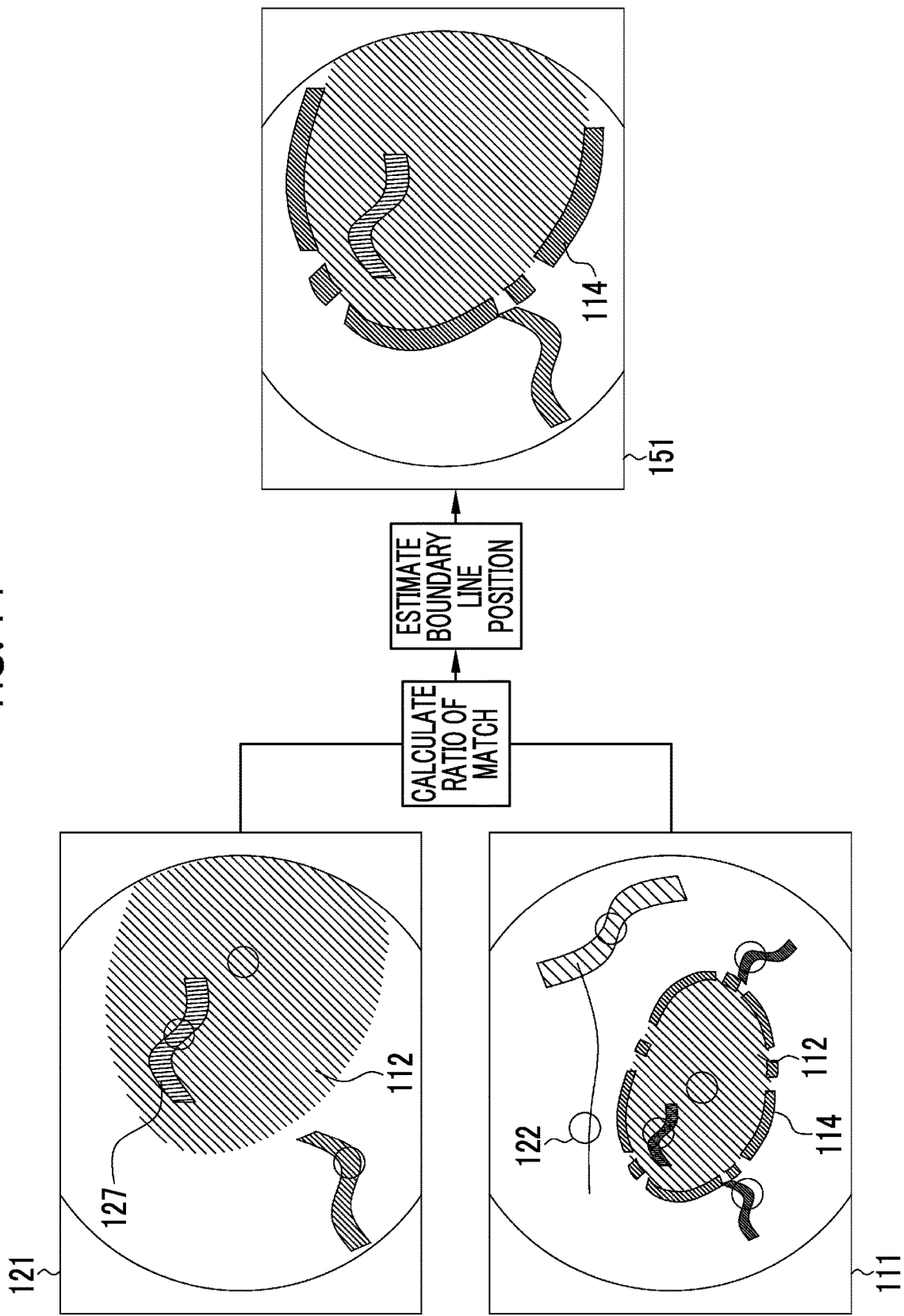
FIG. 14 is an explanatory diagram showing generation of a superimposition image in a case where a captured image is captured to include a part of an abnormal region and a reference image includes the whole of the abnormal region.

As shown in FIG. 14, in a case where the captured image 121 is a medical image captured to include a part of the abnormal region 112 or a structure such as the microvessel 127, and the reference image 111 is a medical image including the entire abnormal region 112, it is preferable to create the superimposition image 151 in which a part of the boundary line associated with the reference image 111 is superimposed on the captured image 121. In this case, the captured image 121 is captured at a higher magnification than that of the reference image 111. In near-view imaging, a small amount of blurring is greatly influenced by the captured image 121. By generating the superimposition image 151 in a case of performing near-view imaging in which the influence of blurring becomes large in real time, it is possible to present an accurate boundary line to a user such as an operator. It is possible to easily check a range of the tumor that has changed between acquisition of the reference image 111 and acquisition of the captured image 121.

Figure 15:
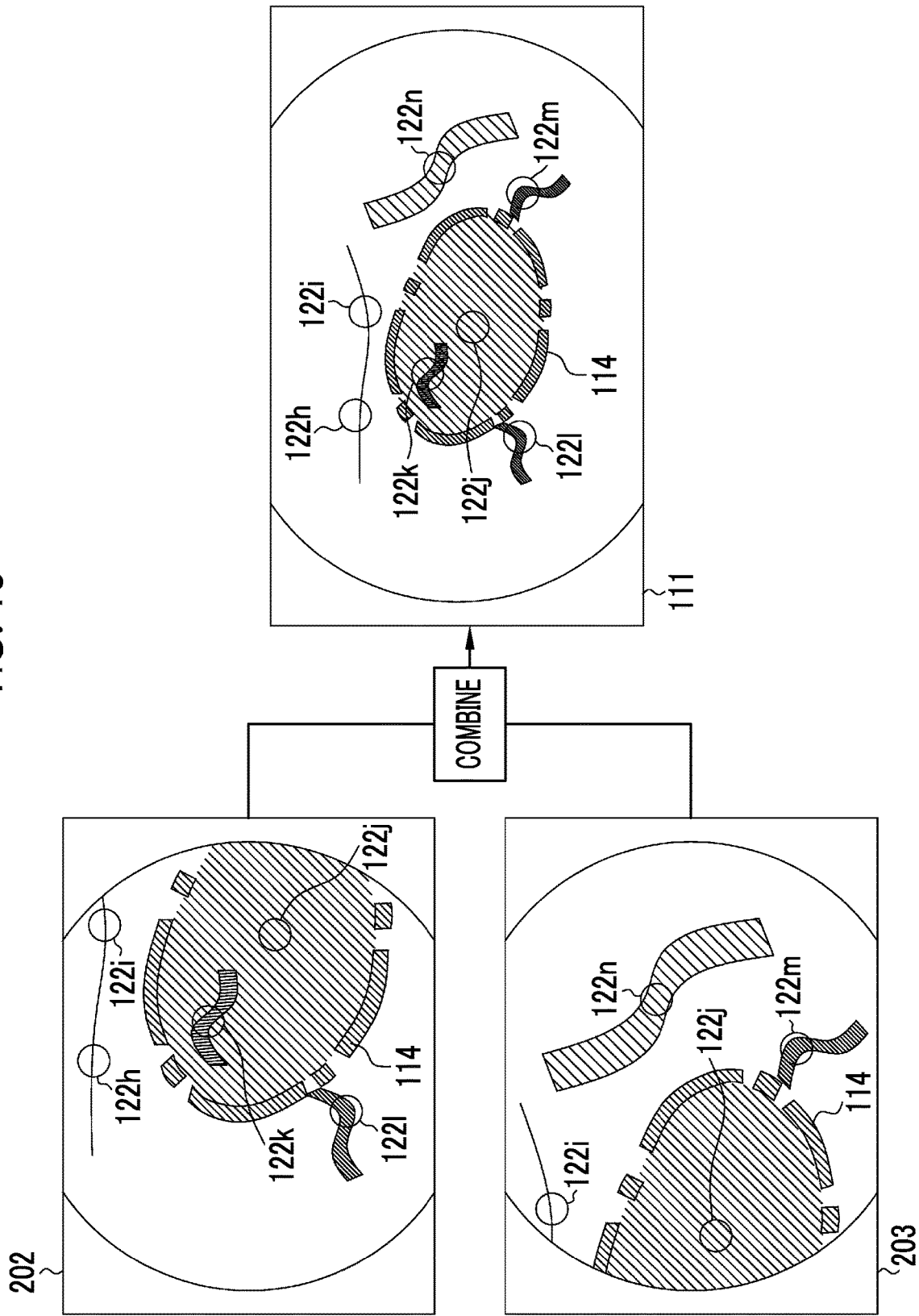
FIG. 15 is an explanatory diagram showing that a reference image is generated by connecting enlarged medical images.

As shown in FIG. 15, it is preferable that a reference image is generated as one reference image 111 by connecting enlarged medical images 202 and 203 that are medical images in which a part of the abnormal region is captured in a near view. Each of the enlarged medical images is associated with the boundary line 114, information related to the boundary line 114, landmarks (indicated by circles 122h, 122i, 122j, 122k, 122l, 122m, and 122n), and information related to the landmarks by an association unit 260 according to a method that will be described later. The enlarged medical image is a still image captured in a near view at a magnification at which a boundary between an abnormal region and a normal region can be distinguished, and is captured under optimum conditions without out-of-focus or halation. By connecting the enlarged medical images to generate the reference image, it is possible to superimpose a high-definition and accurate boundary line obtained in advance on the captured image.

Figure 16:
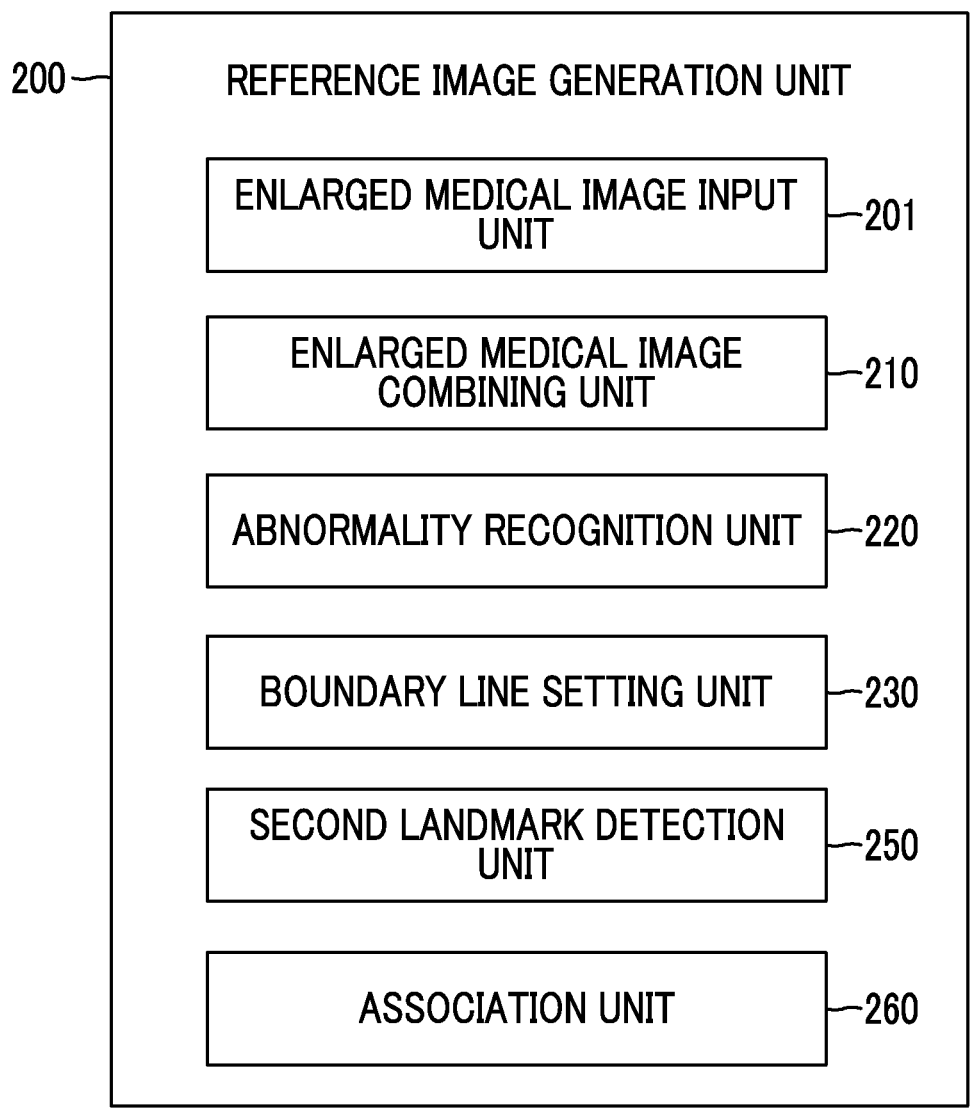
FIG. 16 is a block diagram showing a function of a reference image generation unit in a boundary line display mode.

An example of connecting enlarged medical images to generate a reference image will be described. Connection of the enlarged medical images 202 and 203 is performed after each of the enlarged medical images 202 and 203 is input to the enlarged medical image input unit 201 of the reference image generation unit 200 and is then transmitted to an enlarged medical image combining unit 210 as shown in FIG. 16. The enlarged medical image may be an enlarged captured image that will be described later, or may be a medical image input from the outside of the endoscope system 10. The reference image generation unit 200 includes the enlarged medical image input unit 201, the enlarged medical image combining unit 210, and an abnormality identification unit 220 a boundary line setting unit 230, a second landmark detection unit 250, and the association unit 260, which will be described later.

Figure 17:
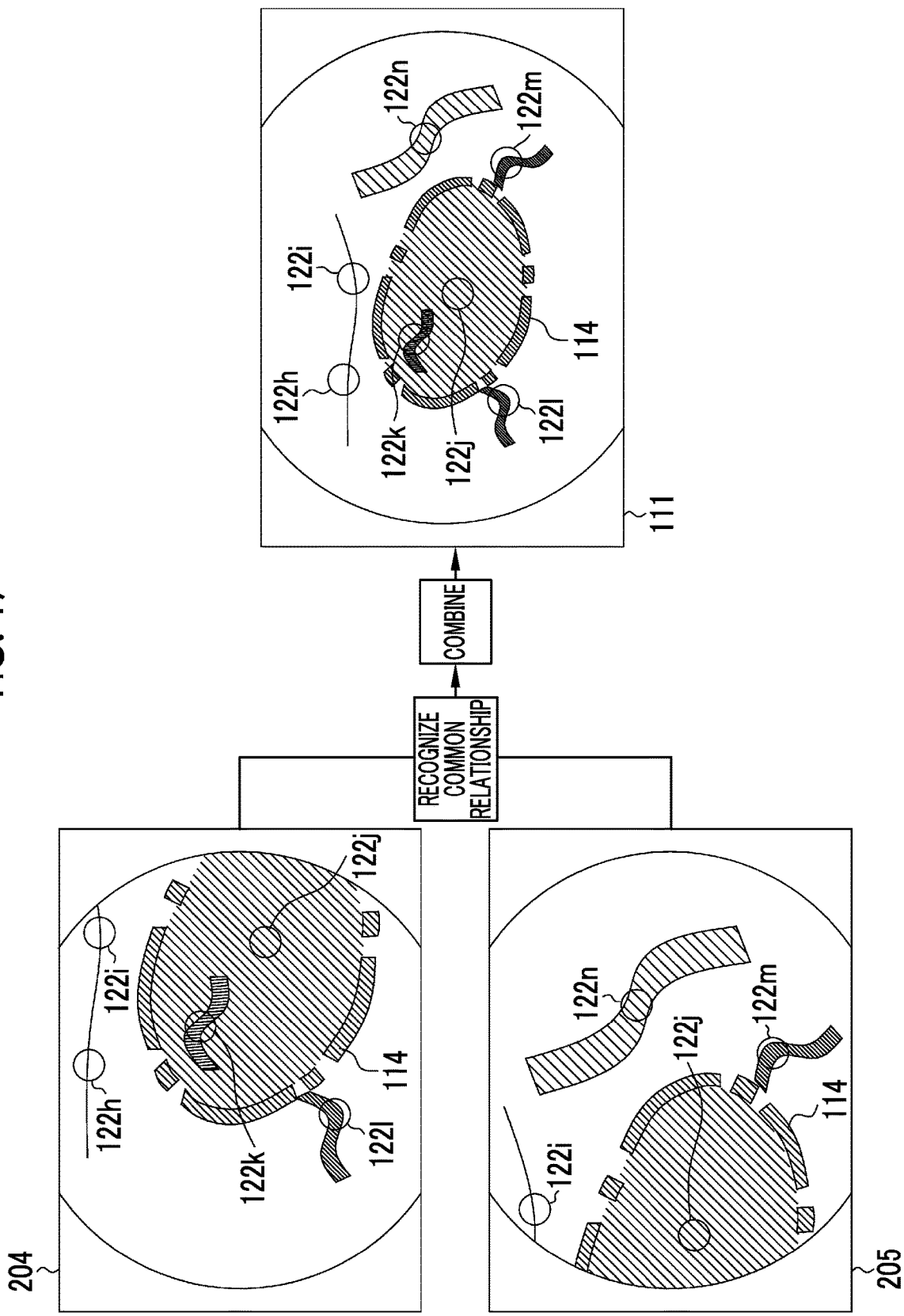
FIG. 17 is an explanatory diagram showing generation of a reference image by connecting enlarged medical images by using a common relationship.

As shown in FIG. 17, a case where the reference image 111 is created from a first enlarged medical image 204 and a second enlarged medical image 205 captured at a position different from that of the first enlarged medical image 204 will be described as an example. In this case, first, the enlarged medical image input unit 201 transmits the first enlarged medical image 204 and the second enlarged medical image 205 to the enlarged medical image combining unit 210. The enlarged medical image combining unit 210 recognizes a common relationship on the basis of landmark information (landmarks are indicated by circles 122h, 122i, 122j, 122k, and 122l) and boundary line information (the boundary line 114 is indicated by a dot chain line) associated with the first enlarged medical image 204, and landmark information (landmarks are indicated by circles 122j, 122j, 122k, 122m, and 122n) and boundary line information (the boundary line 114 is indicated by a dot chain line) associated with the second enlarged medical image, and connects the first enlarged medical image 204 and the second enlarged medical image 205 to generate the reference image on the basis of the common relationship.

The common relationship is a relationship for determining whether or not the pieces of landmark information (landmarks) and the pieces of boundary line information (boundary lines) respectively associated with the first enlarged medical image 204 and the second enlarged medical image 205 are common to (match) each other. The landmark information includes position information of the landmark and a positional relationship between the landmarks. The boundary line information includes a position information of the boundary line.

In a specific example shown in FIG. 17, the reference image 111 is generated on the basis of a common relationship between the landmark information regarding two landmarks indicated by a circle 112i and a circle 112j and boundary line information. In order to combine the enlarged medical images, it is preferable that at least two or more landmarks in each enlarged medical image are common.

In the above specific example, the case where the reference image is created from the first enlarged medical image 204 and the second enlarged medical image 205 has been described as an example, but the present invention is also applicable to a case where there are three or more enlarged medical images, that is, a first enlarged medical image to an Nth enlarged medical image are connected by recognizing a common relationship between the enlarged medical images. With the above configuration, it is possible to generate a reference image by connecting a plurality of enlarged medical images associated with landmark information and boundary line information. Consequently, it is possible to improve the accuracy of a boundary line superimposed on a captured image on the basis of a reference image in which the boundary line is precisely set. Since the number of landmarks associated with one reference image increases, a correspondence relationship between the reference image and the captured image can be estimated with higher accuracy from a positional relationship of the landmarks.

Figure 18:
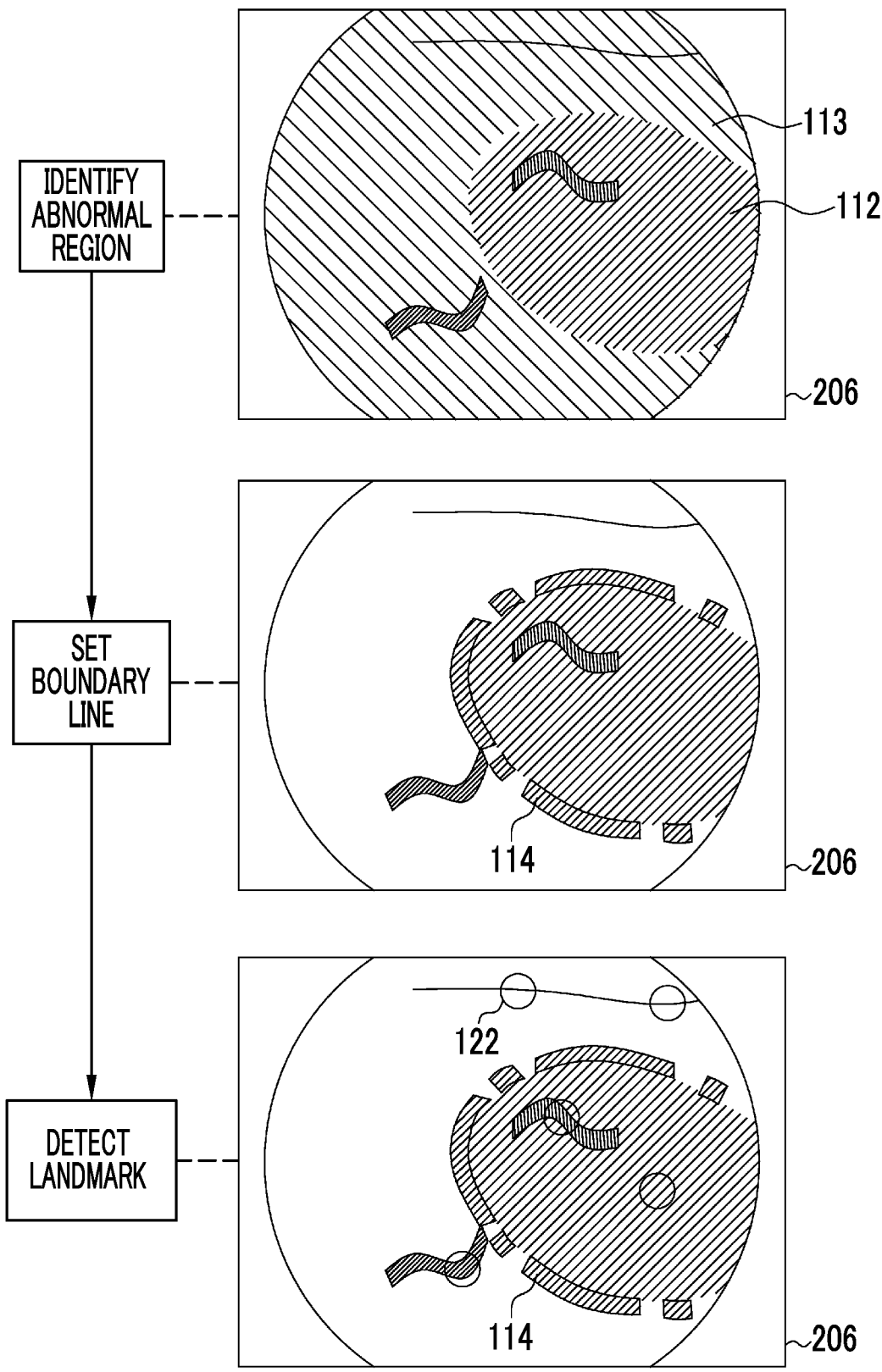
FIG. 18 is an explanatory diagram showing identification of an abnormal region, setting of a boundary line, and detection of a landmark in an enlarged medical image in a case where a boundary line is automatically set.

It is preferable that the boundary line associated with the reference image is set by automatically distinguishing between the abnormal region and the normal region. In this case, the enlarged medical image is transmitted from the enlarged medical image input unit 201 to an abnormality identification unit 220 (refer to FIG. 16). As shown in FIG. 18, the abnormality identification unit 220 identifies the abnormal region 112 and the normal region 113 in the enlarged medical image 206, and the boundary line setting unit 230 (refer to FIG. 16) sets the boundary line 114 and further acquires position information of the boundary line. Next, the second landmark detection unit 250 (refer to FIG. 16) detects the landmark (indicated by the circle 122) from the enlarged medical image 206, and further acquires position information of the landmark and a positional relationship of the landmark. The association unit 260 (refer to FIG. 16) receives the boundary line information (the position information of the boundary line) from the boundary line setting unit 230, and further receives the landmark information (the position information of the landmark and the positional relationship of the landmark) from the second landmark detection unit 250. The association unit 260 associates the enlarged medical image, the boundary line information, and the landmark information with each other, and generates the enlarged medical image as the reference image. The reference image is transmitted from the reference image generation unit 200 to the reference image recording unit 110 and recorded. The enlarged medical image with which the boundary line information and the landmark information are associated may be transmitted to the enlarged medical image combining unit 210 and used to be combined with other enlarged medical images. With the above configuration, the automatically set boundary line information can be used to be superimposed on a captured image.

The abnormality identification unit 220 is preferably a learning model that has learned training medical image data in which an abnormal region and a normal region are identified in advance by using machine learning and has performed learning for identification between the abnormal region and the normal region. Information regarding the abnormal region and the normal region in the training medical image data may be added by a skilled doctor or may be automatically added by a device other than the medical image processing device 11. It is preferable to use deep learning for machine learning to generate a model having performed learning, and, for example, it is preferable to use a multi-layer convolutional neural network. In addition to the deep learning, the machine learning includes a determination tree, a support vector machine, a random forest, regression analysis, supervised learning, semi-unsupervised learning, unsupervised learning, reinforcement learning, deep reinforcement learning, learning using neural networks, a hostile generation network, and the like.

Figure 19:
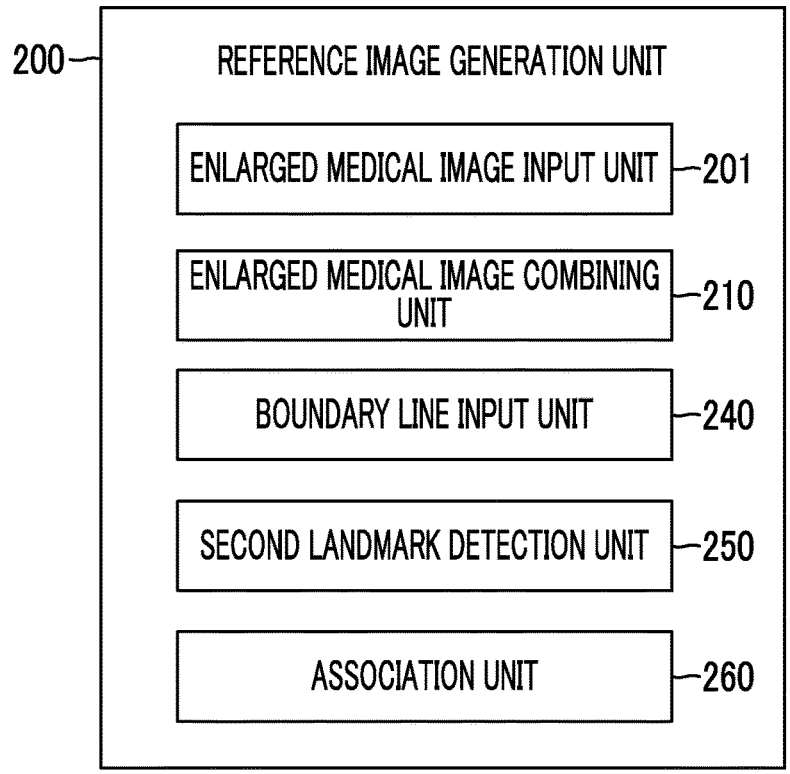
FIG. 19 is a block diagram showing a function of a reference image generation unit in a case where a boundary line is set through a user operation.
Figure 20:
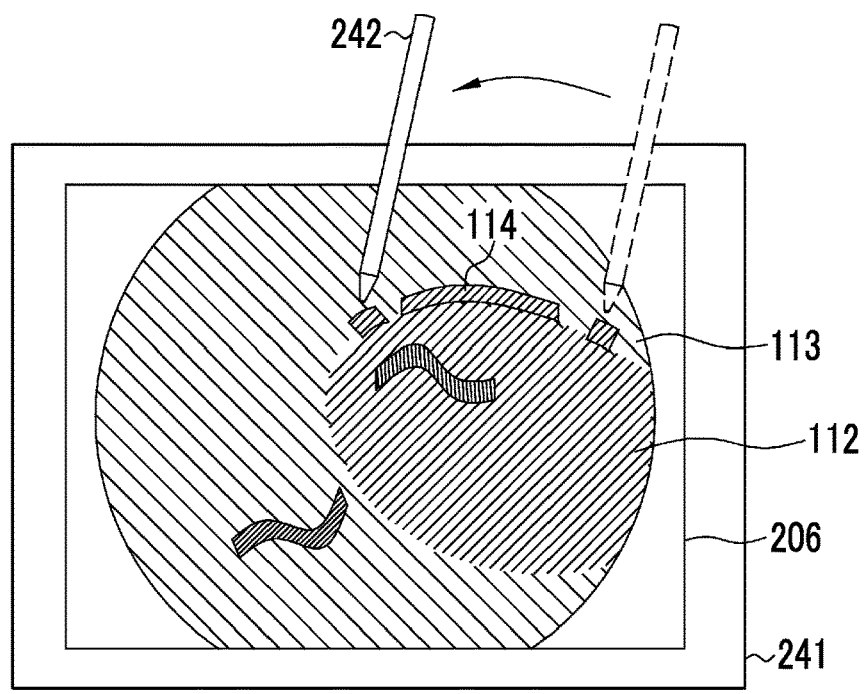
FIG. 20 is an explanatory diagram for setting a boundary line through a user operation.

It is preferable that the boundary line associated with the reference image is set through a user operation. In this case, as shown in FIG. 19, the abnormality identification unit 220 and the boundary line setting unit 230 of the reference image generation unit 200 may be used as a boundary line input unit 240. In a case where the boundary line is set through a user operation, a user such as a doctor determines a boundary between the abnormal region 112 and the normal region 113, and sets a boundary line. For example, as shown in FIG. 20, the boundary line 114 may be drawn with a touch pen 242 for the enlarged medical image 206 displayed on the tablet terminal 241, and the boundary line may be set by giving a boundary line input instruction via a boundary line input button (not shown) or in voice. In a case where the boundary line input instruction is given, position information of the boundary line is automatically acquired. With the above configuration, the boundary line identified by the doctor can be used to be superimposed on a captured image. In this case as well, it is preferable that the second landmark detection unit 250 detects a landmark in the enlarged medical image and acquires landmark information, and, further, the association unit 260 receives boundary line information from the boundary line input unit 240, receives landmark information from the second landmark detection unit 250, associates the enlarged medical image, the boundary line information, and the landmark information with each other, and generates the enlarged medical image as a reference image.

Figure 21:
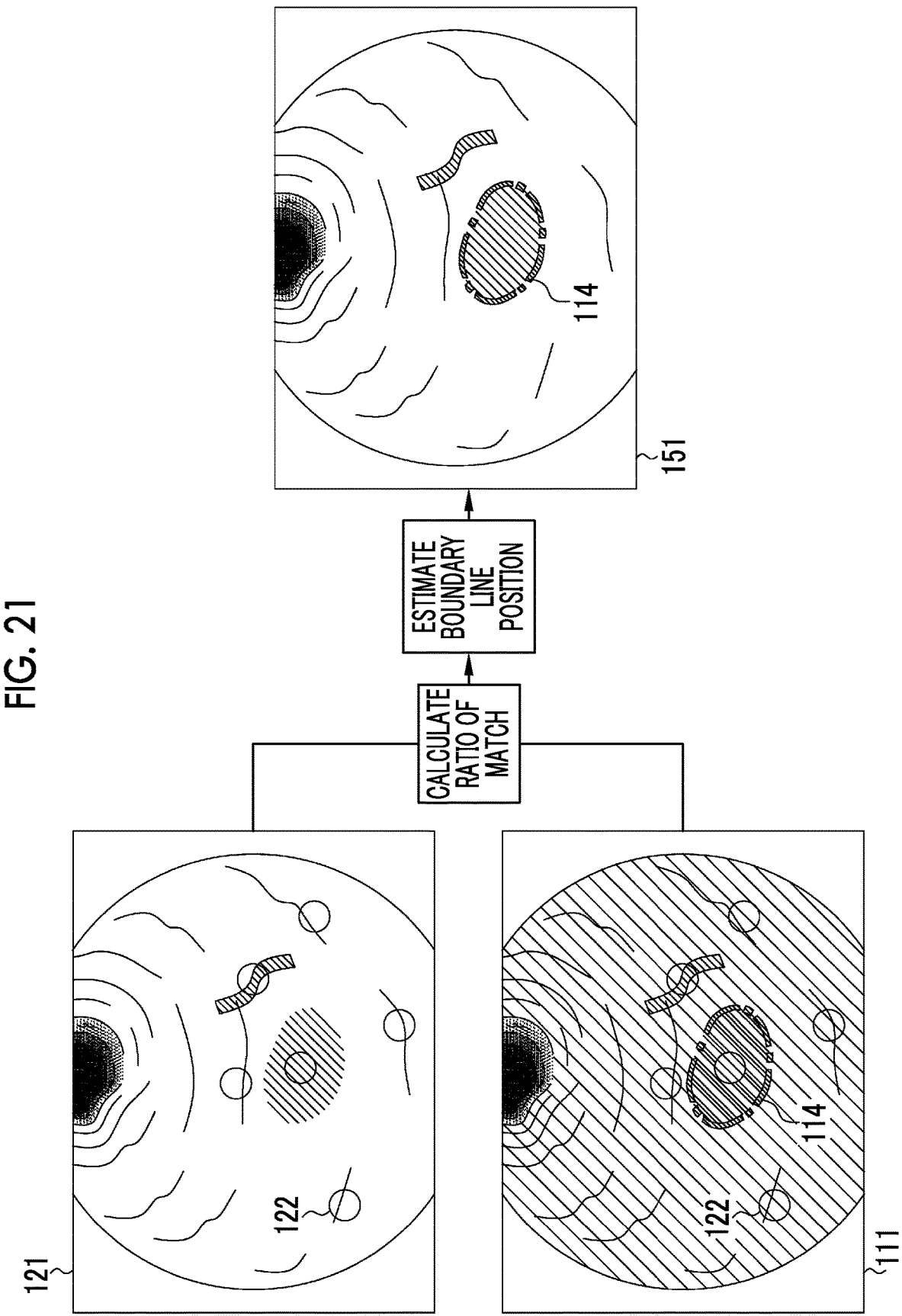
FIG. 21 is an explanatory diagram showing generation of a superimposition image in a case where a reference image is captured by using special light and the captured image is captured by using normal light.

As shown in FIG. 21, it is preferable that the reference image 111 may be a medical image captured by illuminating a subject with special light, and the captured image 121 may be a medical image captured by illuminating a subject with normal light. The special light is illumination light that makes it easy to see a blood vessel or a glandular ductal structure, and makes it easy to recognize a characteristic blood vessel arrangement or a pit pattern of the tumor. Thus, it is easy to determine a boundary between an abnormal region and a normal region in the medical image acquired by using the special light. For the above reasons, it is preferable to use a medical image acquired by using special light as a reference image. On the other hand, normal light is light having a natural hue, and in a case of performing ESD treatment, normal light is used to illuminate a subject. Thus, the captured image is preferably a medical image acquired by using normal light. With the above configuration, it is possible to superimpose a boundary line in a reference image in which a boundary between an abnormal region and a normal region is accurately determined by using special light on a captured image acquired by using normal light.

Figure 22:
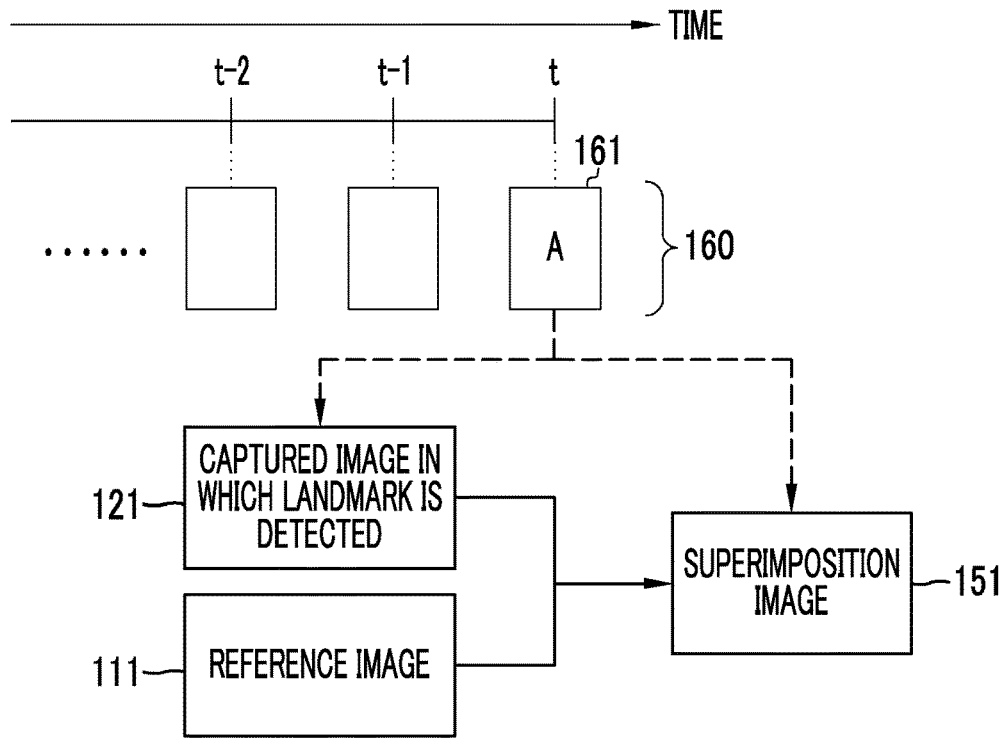
FIG. 22 is an explanatory diagram showing generation of a superimposition image in a case where a captured image for detecting a landmark and a captured image for superimposing a boundary line are captured images captured at the same time.

In a case of superimposing the boundary line associated with the reference image on the captured image, a captured image in which a landmark is detected and a captured image on which a boundary line is superimposed may be the same as or different from each other depending on a processing speed at which the first landmark detection unit 120 detects a landmark from a captured image. It is preferable that the captured image in which a landmark is detected and the captured image on which a boundary line is superimposed are captured images that are captured at the same time point by using a processor having a high processing speed for detecting the landmark. Hereinafter, a specific description will be given. As illustrated in FIG. 22, in a case where a captured image group 160 acquired in a time series is acquired in the order of time point t−2, time point t−1, and time point t, a captured image acquired at time point t is referred to as a captured image A161. In a case where the processing speed for detecting a landmark is high, both the captured image 121 in which the landmark is detected and the captured image on which the boundary line associated with the reference image 111 is superimposed are the captured image A161. In this case, it is possible to obtain a superimposition image in which an accurate boundary line is superimposed in real time with high accuracy.

On the other hand, by using a processor having a low processing speed for detecting a landmark, the captured image in which a landmark is detected and the captured image on which a boundary line is superimposed may be captured images that are captured at different time points.

Figure 23:
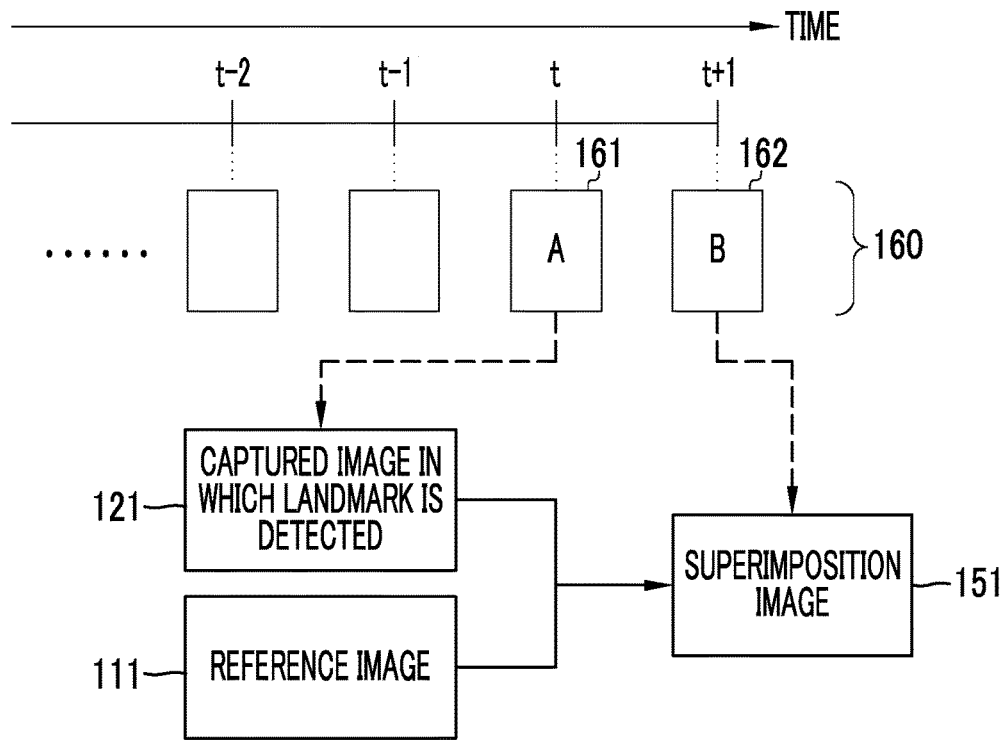
FIG. 23 is an explanatory diagram showing generation of a superimposition image in a case where a captured image for detecting a landmark and a captured image for superimposing a boundary line are captured images captured at different times.

Specifically, as illustrated in FIG. 23, in a case where the captured image group 160 acquired in chronological order is acquired in chronological order of time point t−2, time point t−1, time point t, and time point t+1, a captured image acquired at time point t is referred to as a captured image A161, and a captured image acquired at time point t+1 is referred to as a captured image B162. In a case where a processing speed for detecting a landmark is low, the captured image 121 in which a landmark is detected is the captured image A161, and the captured image on which a boundary line associated with the reference image 111 is superimposed is the captured image B162. In this case, even if a low-speed processor is used, it is possible to obtain a superimposition image in which an accurate boundary line is superimposed in almost real time while ensuring a certain degree of high accuracy.

In FIGS. 21 and 22, a captured image of one frame is acquired at each of time point t−2, time point t−1, time point t, and time point t+1, but captured images of a plurality of frames may be acquired at each time point. For example, there may be a difference of several frames between time point t and time point t+1.

In the boundary line display mode, calculation of a ratio of match between landmarks in the captured image and the reference image is continued until an end instruction is given. In the boundary line display mode, landmarks are sequentially detected and a ratio of match with the reference image is calculated for the captured images acquired in real time, and in a case where the ratio of match is equal to or more than a threshold value, the boundary line is superimposed on the captured image. A series of operations of displaying this boundary line is finished, for example, in a case where marking, incision, or the like on the mucous membrane is ended in ESD, or in a case where an end instruction is given via the user interface 19. Even in a case where a mode is changed via the mode selector switch 12f, an end instruction is regarded to be given, and the calculation of a ratio of match is ended.

Figure 24:
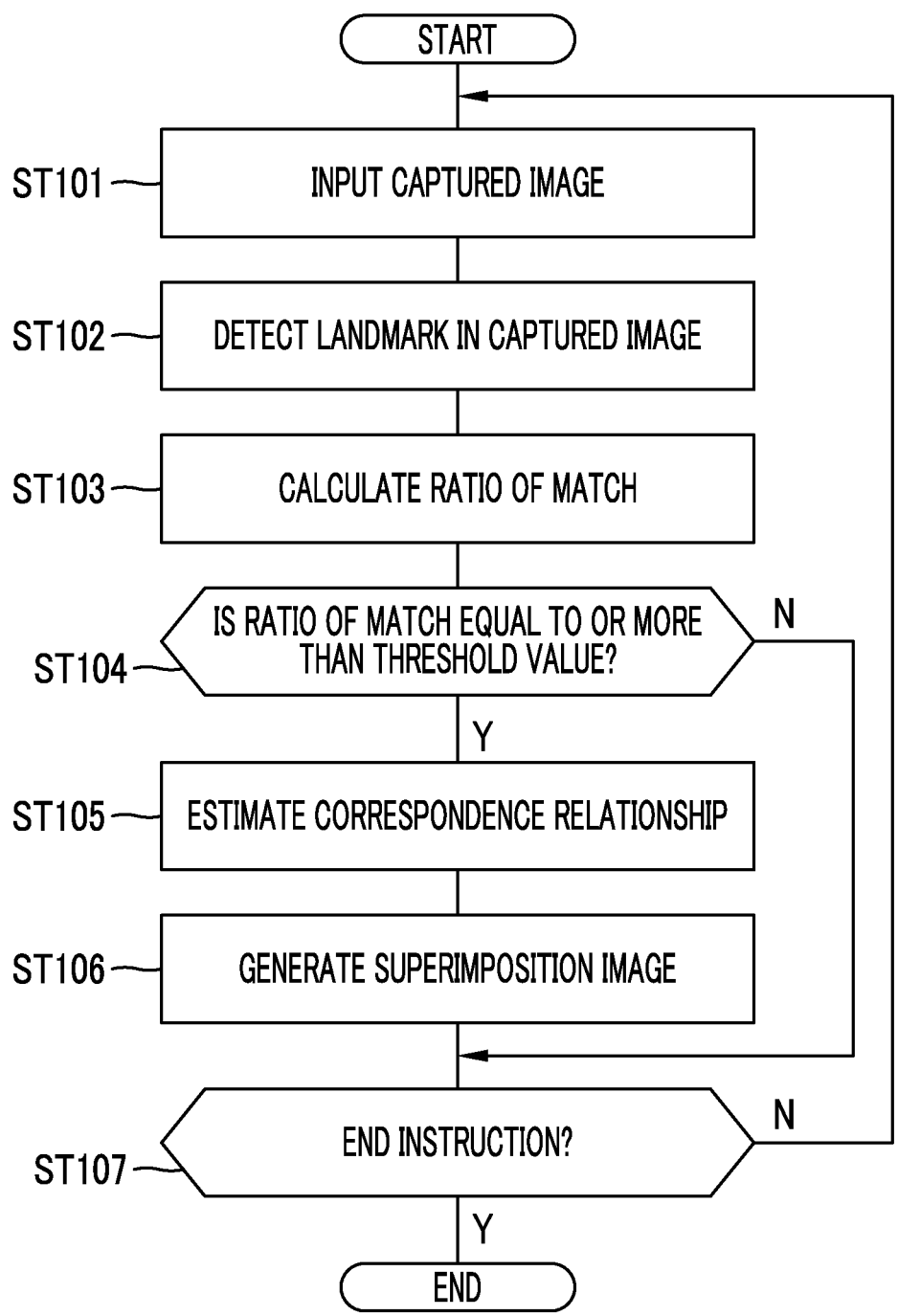
FIG. 24 is a flowchart showing a series of flows in a boundary line display mode.

A flowchart of FIG. 24 shows a series of flows of the boundary line display mode. First, a captured image acquired by the captured image acquisition unit 60 is input to the captured image input unit 100 (ST101). Next, the first landmark detection unit 120 detects a landmark in the captured image (ST102), and the match ratio calculation unit 130 calculates a ratio of match that a value indicating a ratio in which landmarks associated with the reference image are included in landmarks detected from the captured image (ST103). Here, in a case where the ratio of match is less than the threshold value, the process proceeds to selection of whether or not to give an end instruction. On the other hand, in a case where the ratio of match is equal to or more than the threshold value (ST104), a correspondence relationship is estimated by estimating which position in the captured image the boundary line associated with the reference image corresponds to (ST105), and a superimposition image in which the boundary line is superimposed on the captured image is generated (ST106). In a case where the generation of the superimposition image in which the boundary line is superimposed is ended, and an end instruction is given (ST07), the boundary line display mode is ended.

Figure 25:
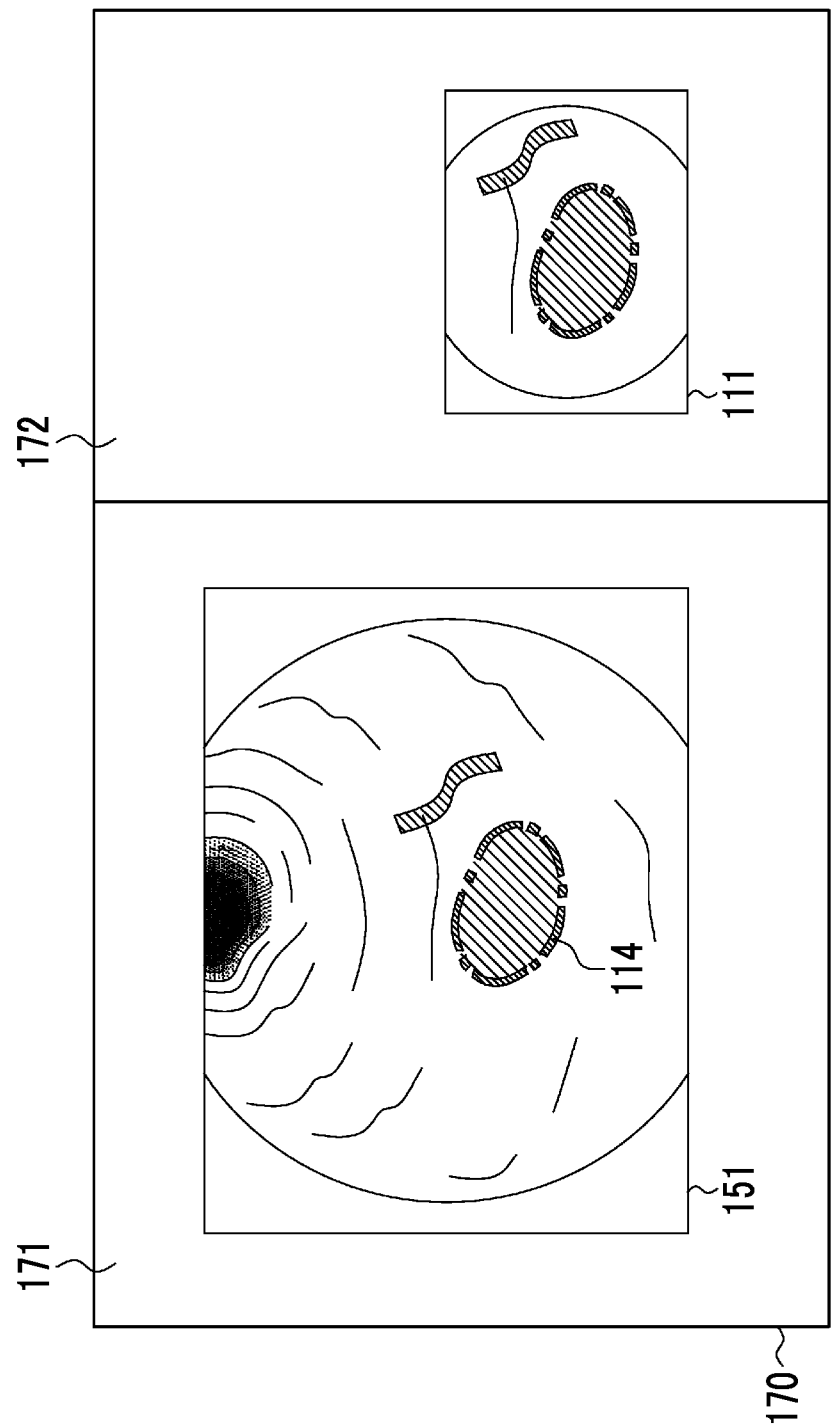
FIG. 25 is an image diagram showing an example of a display image.

It is preferable that the display control unit 150 generates a display image 170 as shown in FIG. 25, displays the superimposition image 151 in a first display section 171 of the display image 170, and displays the reference image 111 in a second display section 172. A display method of the first display section 171 and the second display section 172 is not limited to this. For example, the images may be arranged vertically instead of being arranged horizontally. The endoscope system 10 may include a first display (not shown) and a second display (not shown) different from the first display, and the superimposition image 151 and the reference image 111 may be respectively displayed on different displays.

Hereinafter, the reference image generation mode of generating a reference image from a captured image will be described. The method of generating a reference image from an enlarged medical image has been described above (refer to FIG. 18), but in the case of the reference image generation mode, a reference image is generated from an enlarged medical image as an enlarged captured image captured in a near view such that a boundary between an abnormal region and a normal region can be determined in a captured image acquired in real time.

Figure 26:
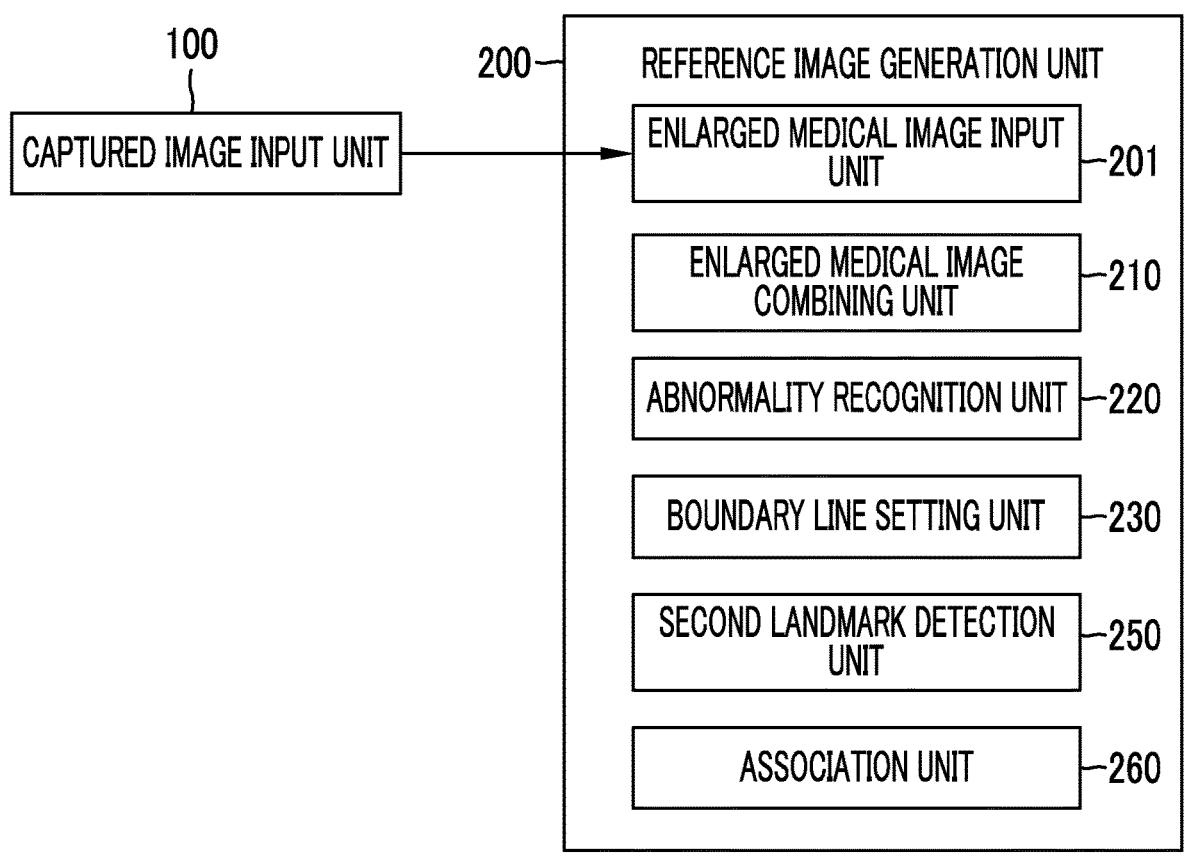
FIG. 26 is a block diagram showing functions of a captured image input unit and a reference image generation unit in the reference image generation mode.
Figure 27:
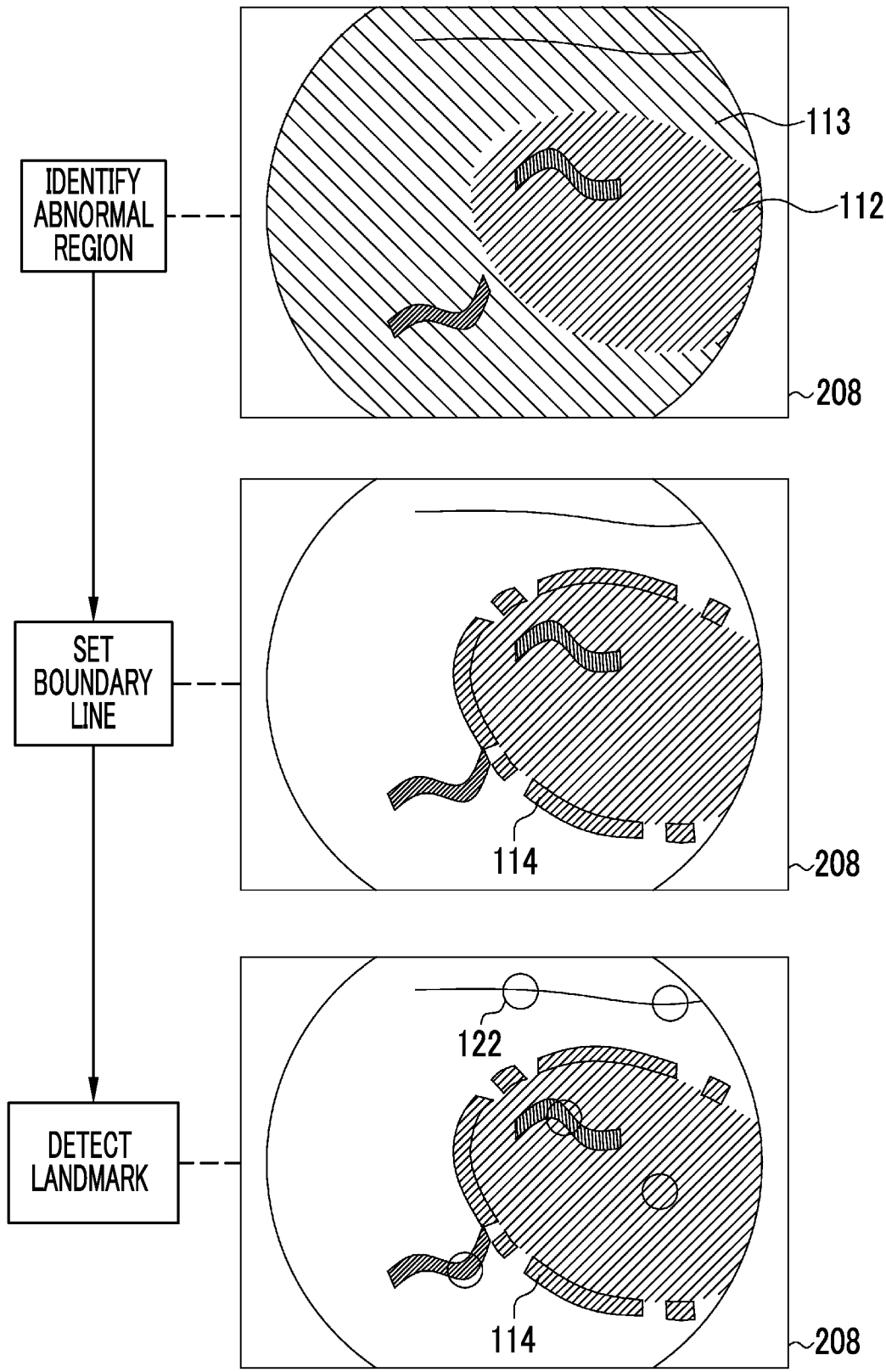
FIG. 27 is an explanatory diagram showing generation of a reference image in a reference image generation mode.

In the case of the reference image generation mode, as shown in FIG. 26, the captured image input unit 100 transmits an input medical image (captured image) to the enlarged medical image input unit 201 of the reference image generation unit 200. The enlarged captured image is preferably a still image acquired by using the still image acquisition instruction switch 12h. The subsequent procedure is the same as in the method of generating a reference image from an enlarged medical image (refer to FIG. 18). The description will be made as follows. The enlarged medical image input unit 201 transmits the enlarged captured image to the abnormality identification unit 220. As shown in FIG. 27, the abnormality identification unit 220 identifies the abnormal region 112 and the normal region 113 in the enlarged captured image 208, and the boundary line setting unit 230 sets the boundary line 114 and acquires position information of the boundary line. Next, the second landmark detection unit 250 detects landmarks (indicated by circles 122) from the enlarged captured image 208, and acquires position information of the landmarks and a positional relationship between the landmarks. The association unit 260 receives the boundary line information (the position information of the boundary line) from the boundary line setting unit 230, and further receives landmark information (the position information of the landmarks and the positional relationship between the landmarks) from the second landmark detection unit 250. The association unit 260 associates the enlarged captured image, the boundary line information, and the landmark information, and generates the enlarged captured image 208 as a reference image. The reference image generated from the enlarged captured image 208 is transmitted from the reference image generation unit 200 to the reference image recording unit 110 and recorded.

The enlarged captured image 208 with which the boundary line information and the landmark information are associated may be transmitted to the enlarged medical image combining unit 210, to be used to be combined with another enlarged captured image with which the boundary line information and the landmark information are associated as a new reference image. With the above configuration, a new reference image can be generated from a captured image, and a boundary line in the generated new reference image can be used to be superimposed on the captured image.

Hereinafter, the boundary line update mode in which a boundary line is set from a captured image and the boundary line is updated in a state in which a superimposition image in which the boundary line associated with a reference image is superimposed on the captured image is displayed will be described. The boundary line update mode is a mode in which a boundary line can be updated through a user instruction in a case where a boundary line displayed on a superimposition image and a boundary line considered by a user who observes the superimposition image are different. This mode is effective, for example, in a case where after the day when the endoscopy is performed once and a reference image is acquired, an infiltration range of the tumor expands when the endoscopy is performed again and a captured image is acquired at the same site where the reference image was acquired, and a new update boundary line is desired to be obtained.

Figure 28:
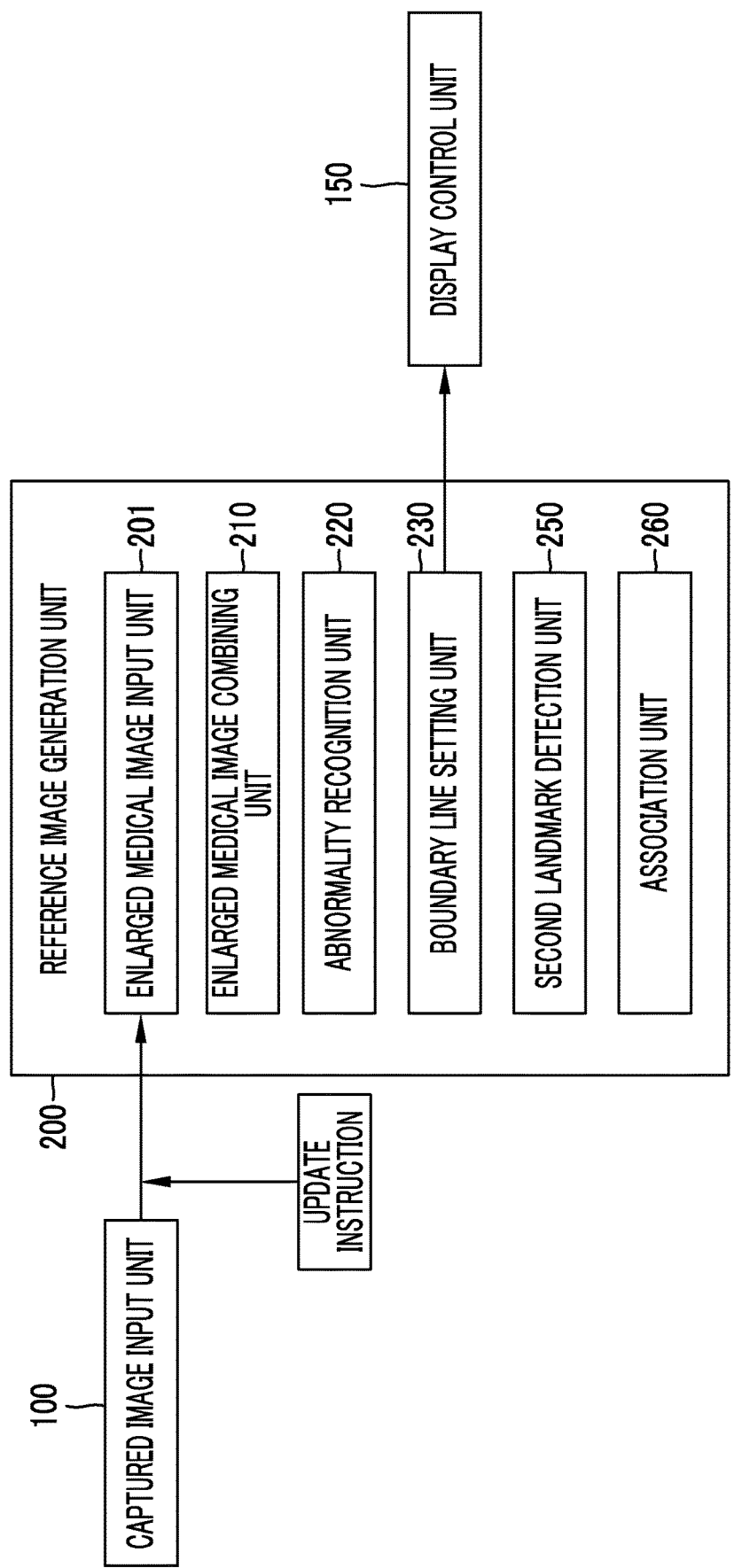
FIG. 28 is a block diagram showing functions of the captured image input unit and the reference image generation unit in a boundary line update mode.
Figure 29:
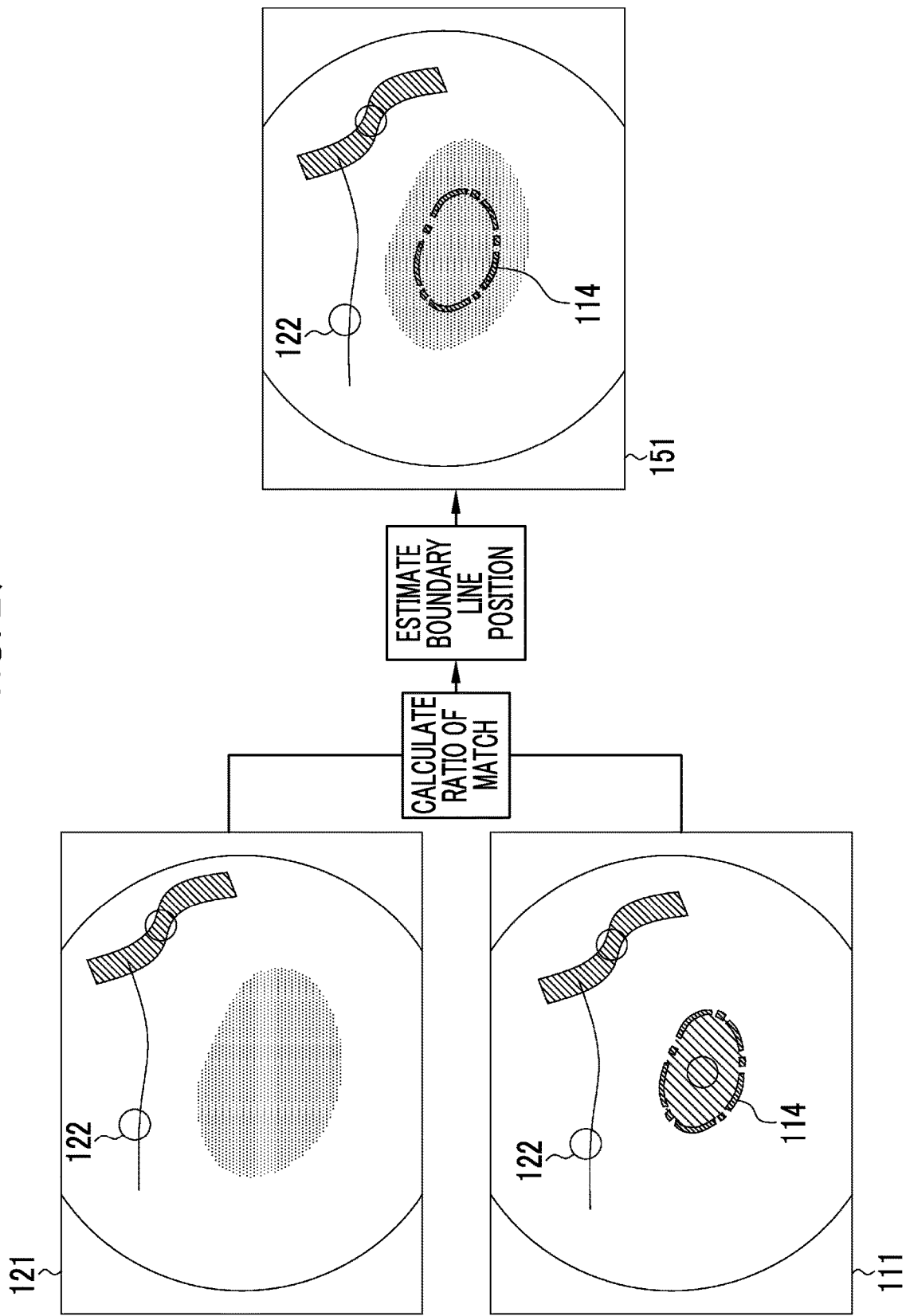
FIG. 29 is an explanatory diagram showing generation of a superimposition image in the boundary line update mode.
Figure 30:
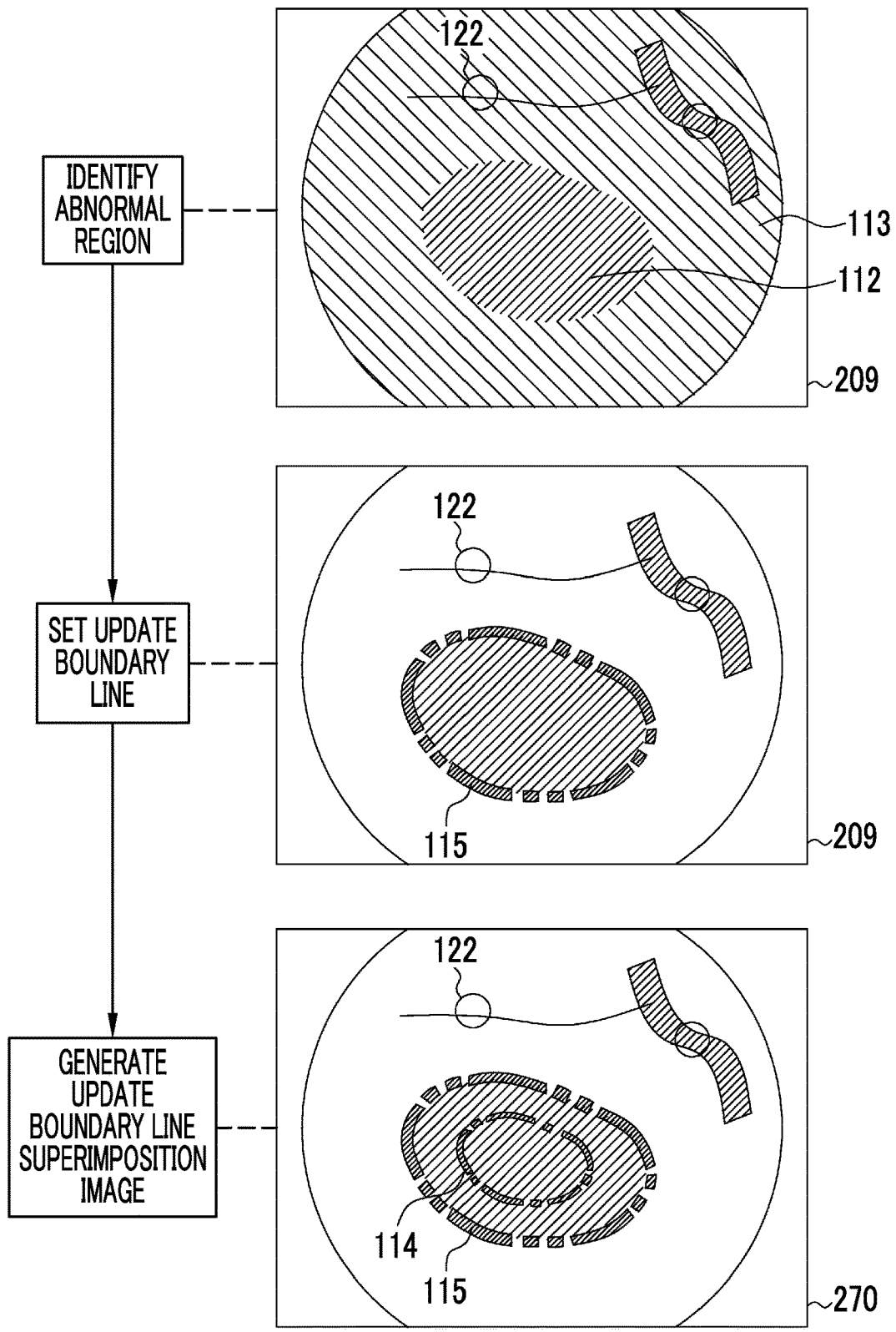
FIG. 30 is an explanatory diagram showing generation of an update boundary line superimposition image.

In the boundary line update mode, first, a superimposition image in which the boundary line associated with the reference image is superimposed on the captured image is generated in the same flow as in the boundary line display mode (refer to the flowchart of FIG. 23). In this case, an update instruction is transmitted to the medical image processing device 11 via the user interface 19 at any timing at which the boundary line is desired to be updated. FIG. 28 is a block diagram showing a function of the medical image processing device 11, and FIGS. 29 and 30 are explanatory diagrams of the boundary line update mode using an image diagram. In a case where an update instruction is received, as shown in FIG. 28, the captured image input unit 100 transmits the captured image 121 (in FIG. 29, a captured image in which a landmark is detected and a captured image on which a boundary line is superimposed are regarded as the same captured image) used to generate the superimposition image 151 on which the boundary line 114 is superimposed as shown in FIG. 29 to the enlarged medical image input unit 201 of the reference image generation unit 200 as the enlarged captured image 209. Next, as shown in FIG. 30, the abnormality identification unit 220 identifies the abnormal region 112 and the normal region 113 in the enlarged captured image 209, and the boundary line setting unit 230 sets an update boundary line 115 (indicated by a two-dot chain line), and acquires position information of the update boundary line. Next, the display control unit 150 receives the position information of the update boundary line from the boundary line setting unit 230, superimposes the update boundary line 115 on the captured image in addition to the boundary line 114 to generate an update boundary line superimposition image 270, and displays the update boundary line superimposition image 270 on the display 17.

Figure 31:
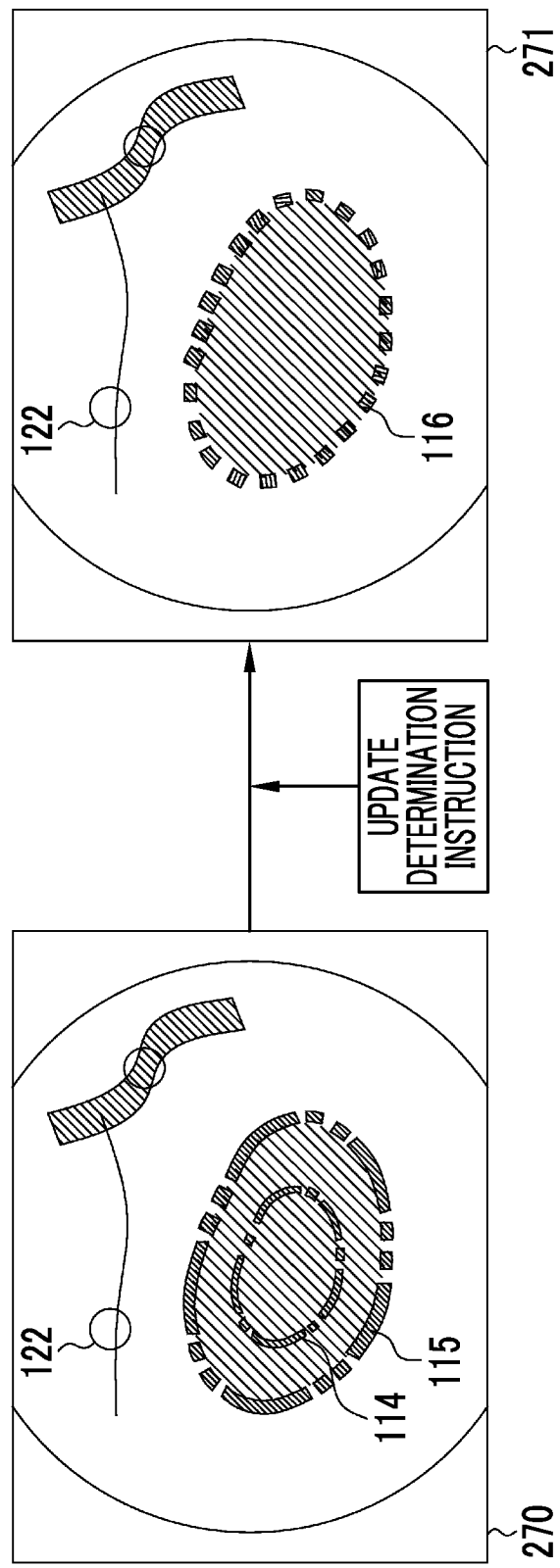
FIG. 31 is an explanatory diagram showing generation of a determined update boundary line superimposition image.

In a case where a user sees the update boundary line superimposition image 270 and determines that the update boundary line may be determined as a new boundary line associated with the captured image, an update determination instruction is transmitted to the medical image processing device 11 via the user interface 19. In a case where the update determination instruction is given, the display control unit 150 updates the boundary line 114 superimposed on the captured image 121 with the update boundary line 115 (indicated by a two-dot chain line) as a determined update boundary line 116 (indicated by a dot line) as shown in FIG. 31, and generates a determined update boundary line superimposition image 271 temperature be displayed on the display 17.

In a case where an update determination instruction is given, an enlarged captured image in which the update boundary line is set may be used as a reference image. In a case where the update determination instruction is given, the second landmark detection unit 250 may detect a landmark code from an enlarged captured image captured image code and acquire position information of the landmark and a positional relationship of the landmark. The association unit 260 receives the position information of the update boundary line from the boundary line setting unit 230, and further receives the landmark information from the second landmark detection unit 250. The association unit 260 associates the enlarged captured image, the update boundary line information, and the landmark information, and generates the enlarged captured image as a reference image. The reference image generated from the enlarged captured image is transmitted from the reference image generation unit 200 to the reference image recording unit 110 and recorded.

The enlarged captured image with which the boundary line information and the landmark information are associated may be transmitted to the enlarged medical image combining unit 210 to be used to be combined with another enlarged captured image. With the above configuration, a reference image can be newly generated from the captured image, and the update boundary line of the newly generated reference image can be used as a boundary line to be superimposed on the captured image.

In the above embodiment, the endoscope 12 uses a flexible endoscope, but the present invention is also suitable in a case where a rigid endoscope (laparoscope/rigid scope) used for surgery or the like is used. In a case where a flexible endoscope is used, a captured image of the superficial mucous membrane of an observation target viewed from the luminal side of the luminal organ is acquired. In a case of using a rigid scope, a captured image of the observation target viewed from the serosa side is acquired.

Figure 32:
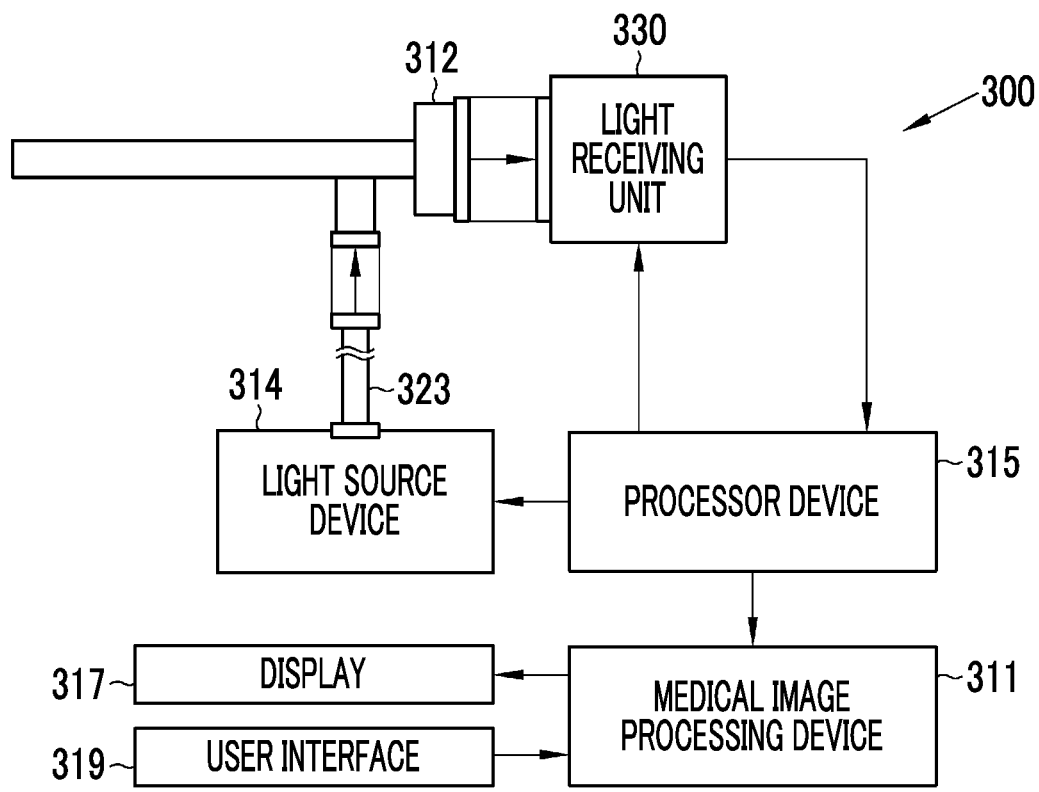
FIG. 32 is an explanatory diagram of a configuration of an endoscope system in a case where a rigid scope is used.

In a case where a rigid scope is used as the endoscope, as shown in FIG. 32, an endoscope system 300 includes a medical image processing device 311, an endoscope 312, a light receiving unit 330, a light source device 314, a processor device 315, a display 317, and a user interface 319. The illumination light from the light source device 314 enters the endoscope 312 via a light guide 323 and illuminates an observation target in the abdominal cavity.

Figure 33:
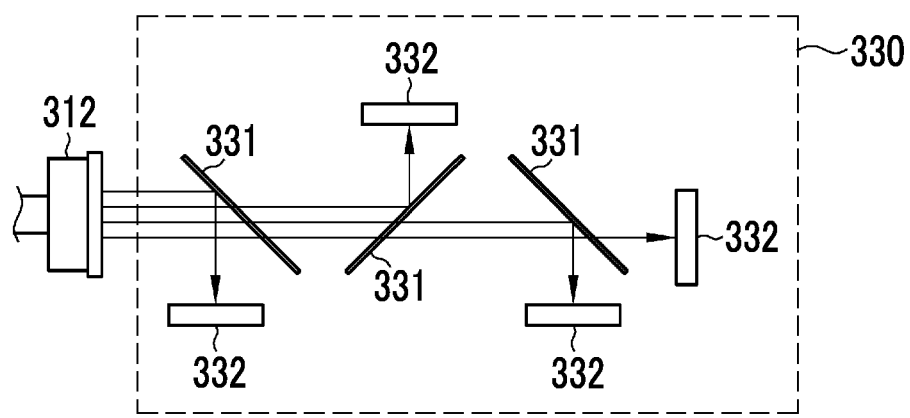
FIG. 33 is an explanatory diagram showing a configuration of a light receiving unit.

As shown in FIG. 33, the light receiving unit 330 includes a spectroscopic element 331 such as a dichroic mirror that disperses the light from the endoscope 312, an image pick-up element 332 such as a CMOS image sensor that senses the dispersed light and picks up an image, and the like, and output an image signal on the basis of reflected light from the observation target. The number of spectroscopic elements 331 may be plural or one, and the spectroscopic elements 331 may or may not be provided. At least one image pick-up element 332 may be provided, or a plurality of image pick-up elements 332 may be provided.

In surgery using a rigid scope, an ICG fluorescence method may be used to classify sentinel lymph nodes or evaluate a blood flow to determine a range of resection. In the ICG fluorescence method, since the biological half-life of ICG is about 3 minutes, a period during which an observation target can be observed by visualizing the ICG after the ICG is administrated into a vein or the like is restricted, it is necessary to repeatedly administer the ICG. On the other hand, in a case where the present invention is used in surgery using a rigid scope as the endoscope 12, during a period in which the ICG is once administered and the observation target can be evaluated, the boundary line setting unit 230 sets a boundary of an observation target, and the second landmark detection unit 250 acquires landmark information and generates a reference image, and thus a boundary line can be reproduced in a captured image that is captured in real time without administration of the ICG thereafter.

In the present embodiment, the example in which the medical image processing device 11 is connected to the endoscope system 10 has been described, but the present invention is not limited to this, and other medical devices such as an ultrasonic imaging device or a radiography device may be used. In the endoscope system 10, a part or the whole of the captured image acquisition unit 60 and/or the first central control unit 55 may be provided in an image processing device that communicates with, for example, the processor device 15 and cooperates with the endoscope system 10. For example, a part or the whole of the captured image acquisition unit 60 and/or the first central control unit 55 may be provided in a diagnosis support device that acquires an image picked up by the endoscope 12 directly from the endoscope system 10 or indirectly from a PACS. A part or the whole of the captured image acquisition unit 60 and/or the first central control unit 55 of the endoscope system 10 may be provided in a medical service support device including the endoscope system 10 and connected to various examination devices such as a first examination device, a second examination device, . . . , and an N-th examination device via a network.

In the present embodiment, hardware structures of processing units executing various processes, such as the captured image acquisition unit 60, the captured image input unit 100, the reference image recording unit 110, the first landmark detection unit 120, the match ratio calculation unit 130, the boundary line position estimation unit 140, the display control unit 150, and the reference image generation unit 200 are various processors as described below. The various processors include a programmable logic device (PLD), that is a processor of which a circuit configuration can be changed after manufacturing, such as a central processing unit (CPU) or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs or a combination of a CPU and an FPGA). A plurality of processing units may be configured with one processor. As an example of configuring a plurality of processing units with one processor, first, there is a form in which one processor is configured with a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured with by using one or more of the above various processors as a hardware structure.

The hardware structure of these various processors is, more specifically, an electric circuit (circuitry) in which circuit elements such as semiconductor elements are combined. The hardware structure of the storage unit is a storage device such as a hard disc drive (HDD) or a solid state drive (SSD).

EXPLANATION OF REFERENCES 10, 300: endoscope system
11, 311: medical image processing device
12: endoscope (flexible endoscope)
12*a*: insertion part
12*b*: operating part
12*c*: bendable part
12*d*: tip part
12*e*: angle knob
12*f*: mode selector switch
12*h*: still image acquisition instruction switch
12*i*: zoom operating part
12*j*: forceps port
14, 314: light source device
15, 315: processor device
17, 317: display
19, 319: user interface
20: light source unit
20*a*: V-LED
20*b*: B-LED
20*c*: G-LED
20*d*: R-LED
21: light source processor
22: optical path coupling portion
23: light guide
30*a*: Illumination optical system
30*b*: image pick-up optical system
31: illumination lens
41: objective lens
42: zoom lens
43: image pick-up sensor
44: image pick-up processor
55: first central control unit
60: captured image acquisition unit
100: captured image input unit
101: second central control unit
110: reference image recording unit
111: reference image
112: abnormal region
113: normal region
114: boundary line
115: update boundary line
116: update determination boundary line
120: first landmark detection unit
121: captured image
122, 122*a*, 122*b*, 122*c*, 122*d*, 122*e*, 122*f*, 122*g*, 122*h*, 122*i*, 122*j*, 122*k*, 122*l*, 122*m*, 122*n*: circle
123: gastrointestinal fold
124, 127: blood vessel
125: lesion
126: link line
130: match ratio calculation unit
140: boundary line position estimation unit
150: display control unit
151: superimposition image
160: captured image group
161: captured image A
162: captured image B
170: display image
171: first display section
172: second display section
200: reference image generation unit
201: enlarged medical image input unit
202, 203, 206: enlarged medical image
204: first enlarged medical image
205: second enlarged medical image
208, 209: enlarged captured image
210: enlarged medical image combining unit
220: abnormality identification unit
230: boundary line setting unit
240: boundary line input unit
241: tablet terminal
242: touch pen
250: second landmark detection unit
260: association unit
270: update boundary line superimposition image 271: determined update boundary line superimposition image
312: endoscope (rigid endoscope)
330: light receiving unit
331: spectroscopic element
332: image pick-up element

What is claimed is:

1. A medical image processing device comprising:
a processor configured to:
acquire a medical image obtained by imaging a subject with an endoscope;
acquire a reference image that is the medical image with which boundary line information related to a boundary line that is a boundary between an abnormal region and a normal region and landmark information related to a landmark that is a characteristic structure of the subject are associated;
acquire a captured image that is the medical image captured in real time;
detect the landmark from the captured image;
calculate a ratio of match between the landmark related to the landmark information that is associated with the reference image and the landmark included in the captured image;
estimate a correspondence relationship between the reference image and the captured image on the basis of the ratio of match and information regarding the landmarks included in the reference image and the captured image; and
generate a superimposition image in which the boundary line associated with the reference image is superimposed on the captured image on the basis of the correspondence relationship.

2. The medical image processing device according to claim 1,
wherein the captured image and the reference image are medical images picked up at the same magnification.

3. The medical image processing device according to claim 1,
wherein the captured image is the medical image captured in a distant view, and the reference image is the medical image captured in a near view.

4. The medical image processing device according to claim 1,
wherein the captured image is the medical image captured to include a part of the abnormal region, and
the reference image is the medical image including the entire abnormal region, and the superimposition image in which a part of the boundary line associated with the reference image is superimposed on the captured image is generated.

5. The medical image processing device according to claim 1,
wherein the reference image is generated by connecting enlarged medical images which are medical images in which a part of the abnormal region is captured in a near view.

6. The medical image processing device according to claim 5,
wherein the processor is configured to:
in a case where the reference image is formed of a first enlarged medical image and a second enlarged medical image captured at a position different from that of the first enlarged medical image,
generate the reference image by connecting the first enlarged medical image and the second enlarged medical image on the basis of a common relationship between the landmark information and the boundary line information associated with the first enlarged medical image and the landmark information and the boundary line information associated with the second enlarged medical image.

7. The medical image processing device according to claim 1,
wherein the processor is configured to:
identify the abnormal region and the normal region; and
set the boundary line.

8. The medical image processing device according to claim 1,
wherein the boundary line is set through a user operation.

9. The medical image processing device according to claim 1,
wherein the reference image is the medical image captured by illuminating the subject with special light, and
the captured image is the medical image captured by illuminating the subject with normal light.

10. The medical image processing device according to claim 1,
wherein the captured image in which the landmark is detected and the captured image on which the boundary line is superimposed are the captured images that are captured at the same time point.

11. The medical image processing device according to claim 1,
wherein the captured image in which the landmark is detected and the captured image on which the boundary line is superimposed are the captured images that are captured at different time points.

12. The medical image processing device according to claim 1,
wherein calculation of the ratio of match is continued until an end instruction is given.

13. The medical image processing device according to claim 1,
wherein the processor is configured to perform control for generating a display image,
displaying the superimposition image in a first display section of the display image, and
displaying the reference image in a second display section different from the first display section of the display image.

14. The medical image processing device according to claim 1,
wherein the processor is configured to:
acquire an enlarged captured image as the captured image;
identify the abnormal region and the normal region included in the enlarged captured image, and sets the boundary line;
detect the landmark from the enlarged captured image; and
generate the reference image by associating the enlarged captured image with the boundary line information related to the boundary line and the landmark information related to the landmark.

15. The medical image processing device according to claim 1,
wherein the processor is configured to:
generate the superimposition image; and
in a case where the abnormal region and the normal region included in the captured image related to the superimposition image on which the boundary line is superimposed are identified in a case where there is an update instruction, and an update boundary line is set with the boundary between the abnormal region and the normal region as the boundary line, and in a case where there is an update determination instruction, update the boundary line superimposed on the captured image with the update boundary line as a determined update boundary line.

16. An endoscope system comprising:

the medical image processing device according to claim 1; and the endoscope.

17. An operation method for a medical image processing device, comprising:

a step of acquiring a medical image obtained by imaging a subject with an endoscope;

a step of acquiring a reference image that is the medical image with which boundary line information related to a boundary line that is a boundary between an abnormal region and a normal region and landmark information related to a landmark that is a characteristic structure of the subject are associated;

a step of acquiring a captured image that is the medical image captured in real time;

a step of detecting the landmark from the captured image;

a step of calculating a ratio of match between the landmark related to the landmark information that is associated with the reference image and the landmark included in the captured image;

a step of estimating a correspondence relationship between the reference image and the captured image on the basis of the ratio of match and information regarding the landmarks included in the reference image and the captured image; and a step of generating a superimposition image in which the boundary line associated with the reference image is superimposed on the captured image on the basis of the correspondence relationship.

* * * * *